(12) United States Patent  (10) Patent No.: US 8,911,486 B1
Drnek et al.  (45) Date of Patent: Dec. 16, 2014

(54) IMPLANTABLE DEVICES FOR THERMAL THERAPY AND RELATED METHODS

(71) Applicant: Neuraxis, LLC, Traverse City, MI (US)

(72) Inventors: Michael Drnek, Hampstead, NH (US); Dan Farley, Traverse City, MI (US); John Sullivan, Pelham, NH (US)

(73) Assignee: Neuraxis, LLC, Traverse City, MI (US)

( * ) Notice: Subject to any disclaimer, the term of this patent is extended or adjusted under 35 U.S.C. 154(b) by 0 days.

(21) Appl. No.: 14/276,265

(22) Filed: May 13, 2014

Related U.S. Application Data

(60) Provisional application No. 61/878,168, filed on Sep. 16, 2013.

(51) Int. Cl.
  *A61F 7/12* (2006.01)
  *A61B 17/70* (2006.01)
  *A61B 18/00* (2006.01)
  *A61F 7/00* (2006.01)

(52) U.S. Cl.
  CPC ............... *A61F 7/12* (2013.01); *A61B 17/7083* (2013.01); *A61B 2018/00339* (2013.01); *A61F 2007/0059* (2013.01)
  USPC ................. 607/113; 606/27; 606/30; 606/31; 606/102; 606/246; 607/96

(58) Field of Classification Search
  USPC .......................... 606/246, 27–31; 607/96–114
  See application file for complete search history.

(56) References Cited

U.S. PATENT DOCUMENTS

| | | | |
|---|---|---|---|
| 3,369,550 A | 2/1968 | Thomas | |
| 4,745,922 A | 5/1988 | Taylor | |
| 4,781,193 A | 11/1988 | Pagden | |
| 4,784,126 A | 11/1988 | Hourahane | |
| 5,108,390 A | 4/1992 | Potocky et al. | |
| 5,196,015 A | 3/1993 | Neubardt | |
| 5,415,624 A | 5/1995 | Williams | |
| 5,433,739 A * | 7/1995 | Sluijter et al. | 607/99 |
| 5,474,558 A | 12/1995 | Neubardt | |

(Continued)

FOREIGN PATENT DOCUMENTS

WO  2009/103758 A2  8/2009

OTHER PUBLICATIONS

Hansebout et al., Local cooling for traumatic spinal cord injury: outcomes in 20 patients and review of the literature. J Neurosurg: Spine. Mar. 14, 2014, pp. 1-12.

(Continued)

*Primary Examiner* — Jerry Cumberledge
(74) *Attorney, Agent, or Firm* — Nutter McClennen & Fish LLP

(57) ABSTRACT

Methods and devices are disclosed herein that generally involve applying thermal therapy to tissue (e.g., localized cooling or heating of tissue). In some embodiments, tissue can be cooled or heated by implanting a malleable or deformable thermal device in proximity to the targeted tissue. The thermal device can be left in place following surgery to facilitate application of post-surgical thermal therapy. In some embodiments, the thermal device can be removed post-surgery in a minimally- or non-invasive manner. The thermal device can be connectionless or can include penetrable regions, pre-attached tubing, or detachable connectors to facilitate application of cooling or heating means to the device. Methods are disclosed for utilizing thermal devices and for carrying out various treatment regimens that involve cooling or heating tissue using such devices.

28 Claims, 17 Drawing Sheets

(56) References Cited

U.S. PATENT DOCUMENTS

| | | | |
|---|---|---|---|
| 5,531,776 A | 7/1996 | Ward et al. | |
| 5,549,559 A | 8/1996 | Eshel | |
| 5,571,147 A | 11/1996 | Sluijter et al. | |
| 5,616,143 A | 4/1997 | Schlapfer et al. | |
| 5,693,099 A | 12/1997 | Harle | |
| 5,855,588 A * | 1/1999 | Young | 606/190 |
| 5,899,898 A | 5/1999 | Arless et al. | |
| 6,238,427 B1 | 5/2001 | Matta | |
| 6,343,644 B1 | 2/2002 | Huang et al. | |
| 6,613,044 B2 | 9/2003 | Carl | |
| 6,629,975 B1 | 10/2003 | Kilpela et al. | |
| 6,699,240 B2 | 3/2004 | Francischelli | |
| 6,733,442 B1 | 5/2004 | Larnard | |
| 6,749,605 B2 | 6/2004 | Ashley et al. | |
| 6,796,985 B2 | 9/2004 | Bolger et al. | |
| 6,818,011 B2 | 11/2004 | Dobak, III | |
| 6,899,694 B2 | 5/2005 | Kadziauskas et al. | |
| 7,044,946 B2 | 5/2006 | Nahon et al. | |
| 7,144,394 B2 | 12/2006 | Carl | |
| 7,182,726 B2 * | 2/2007 | Williams et al. | 600/3 |
| 7,220,951 B2 | 5/2007 | Truckai et al. | |
| 7,241,297 B2 | 7/2007 | Shaolian et al. | |
| 7,347,856 B2 | 3/2008 | Wittenberger et al. | |
| 7,449,019 B2 | 11/2008 | Uchida et al. | |
| 7,645,282 B2 | 1/2010 | Huxel et al. | |
| 7,651,496 B2 | 1/2010 | Keegan et al. | |
| 7,722,620 B2 | 5/2010 | Truckai et al. | |
| 7,819,826 B2 * | 10/2010 | Diederich et al. | 601/3 |
| 7,819,860 B2 | 10/2010 | Wittenberger et al. | |
| 8,348,952 B2 | 1/2013 | Sanders et al. | |
| 8,523,930 B2 | 9/2013 | Saunders et al. | |
| 8,641,609 B2 | 2/2014 | Hestad et al. | |
| 8,721,642 B1 | 5/2014 | Sullivan | |
| 2002/0095144 A1 | 7/2002 | Carl | |
| 2003/0018331 A1 | 1/2003 | Dycus et al. | |
| 2003/0216721 A1 | 11/2003 | Diederich et al. | |
| 2004/0102825 A1 | 5/2004 | Daoud | |
| 2004/0210286 A1 | 10/2004 | Saadat | |
| 2005/0065584 A1 | 3/2005 | Schiff et al. | |
| 2005/0149007 A1 | 7/2005 | Carl | |
| 2006/0015160 A1 | 1/2006 | Larnard | |
| 2006/0241576 A1 | 10/2006 | Diederich et al. | |
| 2007/0050002 A1 | 3/2007 | Elefteriades | |
| 2007/0162007 A1 | 7/2007 | Shoham | |
| 2007/0191831 A1 | 8/2007 | Sanders et al. | |
| 2007/0198050 A1 * | 8/2007 | Ravenscroft et al. | 606/200 |
| 2007/0225781 A1 * | 9/2007 | Saadat et al. | 607/105 |
| 2007/0233148 A1 | 10/2007 | Truckai et al. | |
| 2007/0233226 A1 | 10/2007 | Kochamba et al. | |
| 2007/0233249 A1 | 10/2007 | Shadduck | |
| 2007/0260232 A1 | 11/2007 | Carl | |
| 2007/0260250 A1 | 11/2007 | Wisnewski et al. | |
| 2008/0065062 A1 | 3/2008 | Leung et al. | |
| 2008/0065083 A1 | 3/2008 | Truckai et al. | |
| 2008/0154373 A1 | 6/2008 | Protopsaltis et al. | |
| 2008/0249532 A1 | 10/2008 | Schoutens et al. | |
| 2008/0269761 A1 | 10/2008 | Truckai et al. | |
| 2008/0294222 A1 | 11/2008 | Schechter | |
| 2009/0036893 A1 | 2/2009 | Kartalian et al. | |
| 2010/0312318 A1 | 12/2010 | D'Ambrosio et al. | |
| 2011/0034975 A1 * | 2/2011 | Ferree | 607/105 |
| 2011/0066216 A1 | 3/2011 | Ting et al. | |
| 2011/0282418 A1 | 11/2011 | Saunders et al. | |
| 2012/0065733 A1 | 3/2012 | Wieder | |
| 2012/0221059 A1 | 8/2012 | Mollman et al. | |
| 2012/0288848 A1 | 11/2012 | Latham et al. | |
| 2013/0261507 A1 * | 10/2013 | Diederich et al. | 601/2 |
| 2013/0281995 A1 | 10/2013 | Saunders et al. | |

OTHER PUBLICATIONS

Invitation to Pay Additional Fees in International Application No. PCT/US2014/37825. mailed Sep. 30, 2014 (3 pages).

* cited by examiner

IMPLANTABLE DEVICES FOR THERMAL THERAPY AND RELATED METHODS

CROSS-REFERENCE TO RELATED APPLICATIONS

This application claims the benefit of U.S. Provisional Application No. 61/878,168, filed Sep. 16, 2013, which is hereby incorporated by reference herein in its entirety.

FIELD

Implantable devices for applying thermal therapy and methods relating thereto are disclosed herein.

BACKGROUND

According to the National Spinal Cord Injury Statistical Center, there are more than 259,000 people living with a spinal cord injury in the United States. Traumatic spinal cord injury afflicts around 15,000 people in the United States each year. Approximately 12,000 survive the cord injury with a neurological deficit, which is commonly a severe, disabling physical impairment and mental burden. Long-term care for cord injuries costs an estimated $9.7 billion annually in the United States.

Application of certain degrees of hypothermia to a patient's spine and spinal cord after a spinal cord injury can lead to benefits, such as a reduction of the metabolic demand of spinal cord cells, reduction of edema, added tolerance to hypoxia/ischemia, and ultimately a reduction in spinal cord tissue damage or cell death. Realizing these benefits could mean the difference between quadriplegia and being able to use one's arms. The use of a cooling effect for these purposes can be referred to as therapeutic hypothermia.

Besides traumatic spinal cord injury, the spinal cord can be injured due to surgical procedures such as abdominal aneurysm repair, wherein blood flow to the spinal cord is reduced. This lack of blood flow, also known as ischemia, can cause cellular damage to the spinal cord. Local cooling of the spinal cord can decrease the incidence of spinal cord injury in abdominal aneurysm surgery. Nerve roots or any member of the central nervous system in the spine can also become damaged from trauma and/or surgical insult, and can cause neurologic deficits and/or significant patient pain. It will be appreciated that the spinal cord and nerves can become injured through any number of means.

Existing methods for cooling the spine involve systemic cooling of the entire body. Such treatments carry a number of disadvantages. For one thing, systemic cooling techniques lack the ability to specifically target the injured tissue and, as a result, other unrelated tissue can be damaged or destroyed by the cooling. Systemic cooling can also cause a wide variety of side effects. In addition, the degree to which the body can be cooled systemically is very limited, and it is difficult to precisely control the degree to which the body is cooled in systemic approaches. Body temperature changes using systemic techniques also tend to occur very slowly, which can undesirably delay administration of a cooling effect to the injured tissue.

In some instances it can be desirable to apply localized heating or therapeutic hyperthermia to a patient.

There is a continual need for improved methods and devices for applying thermal therapy.

SUMMARY

Methods and devices are disclosed herein that generally involve applying thermal therapy to tissue (e.g., localized cooling or heating of tissue), and in particular applying thermal therapy to the spinal canal, tissue disposed within the spinal canal, and/or nerve roots extending from the spinal canal. In some embodiments, tissue can be cooled or heated by implanting a malleable or deformable thermal device in proximity to the targeted tissue. The thermal device can be left in place following surgery to facilitate application of post-surgical thermal therapy. In some embodiments, the thermal device can be removed post-surgery in a minimally- or non-invasive manner. The thermal device can be connectionless or can include penetrable regions, pre-attached tubing, or detachable connectors to facilitate application of cooling or heating means to the device. Methods are disclosed for utilizing thermal devices and for carrying out various treatment regimens that involve cooling or heating tissue using such devices.

In some embodiments, a method of applying thermal therapy to tissue includes forming a tissue opening in a patient to access a target site within the patient, passing a thermal device through the tissue opening, placing the thermal device at the target site, closing the tissue opening with the thermal device at the target site, and after closing the tissue opening, applying or continuing to apply thermal therapy to the target site through the thermal device, wherein the thermal device comprises a malleable pad.

In some embodiments, a method of applying thermal therapy to tissue includes forming a tissue opening in a patient to access a target site within the patient, passing a thermal device through the tissue opening, placing the thermal device at the target site, closing the tissue opening with the thermal device at the target site, and after closing the tissue opening, applying or continuing to apply thermal therapy to the target site through the thermal device, wherein the thermal device comprises a connector having a plurality of exposed loops of fluid tubing extending therefrom, and wherein placing the thermal device comprises placing the loops across the target site.

In some embodiments, a system includes an implantable pad having an outer membrane that defines a cavity therein and that includes a penetrable region, a connector insertable through the penetrable region, the connector including a fluid inlet conduit and a fluid outlet conduit which are placed in fluid communication with the cavity when the connector is inserted through the penetrable region, and a thermal source coupled to the connector and configured to circulate heated or chilled fluid through a fluid path defined by the fluid inlet conduit, the cavity, and the fluid outlet conduit to apply thermal therapy to anatomy disposed in proximity to the pad.

In some embodiments, a system includes an implantable pad having an outer membrane that defines a cavity therein, a fluid inlet conduit extending from the pad and in fluid communication with the cavity, a fluid outlet conduit extending from the pad and in fluid communication with the cavity, and a thermal source coupled to the fluid inlet conduit and the fluid outlet conduit and configured to circulate heated or chilled fluid through a fluid path defined by the fluid inlet conduit, the cavity, and the fluid outlet conduit to apply thermal therapy to anatomy disposed in proximity to the pad.

In some embodiments, a system includes an implantable pad having an outer membrane that defines a cavity therein and that includes a port, the port including a mating interface, a connector having a mating interface configured to be selectively coupled to the mating interface of the port, the connector including a fluid inlet conduit and a fluid outlet conduit which are placed in fluid communication with the cavity when the connector is coupled to the port, and a thermal source coupled to the connector and configured to circulate heated or chilled fluid through a fluid path defined by the fluid inlet conduit, the cavity, and the fluid outlet conduit to apply thermal therapy to anatomy disposed in proximity to the pad.

In some embodiments, a system includes a connector that includes a fluid inlet conduit and a fluid outlet conduit extending therethrough, a plurality of exposed loops of tubing extending from a distal end of the connector, each of said loops having a first end in fluid communication with the fluid inlet conduit and a second end in fluid communication with the fluid outlet conduit, and a thermal source coupled to the connector and configured to circulate heated or chilled fluid through a fluid path defined by the fluid inlet conduit, the plurality of loops of tubing, and the fluid outlet conduit to apply thermal therapy to anatomy disposed in proximity to the loops of tubing.

The present invention further provides methods, systems, and devices as claimed.

BRIEF DESCRIPTION OF THE DRAWINGS

The invention will be more fully understood from the following detailed description taken in conjunction with the accompanying drawings, in which.

DETAILED DESCRIPTION

Figure 1:
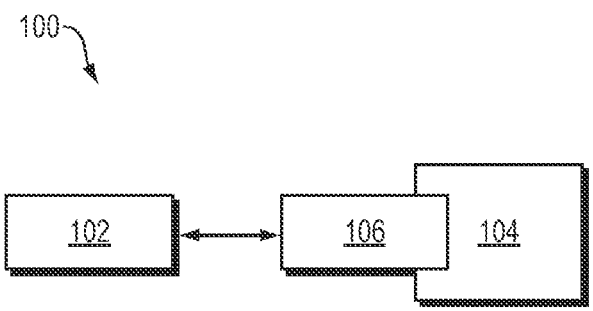
FIG. 1 is a schematic view of a system for applying thermal therapy.

Methods and devices are disclosed herein that generally involve applying thermal therapy to tissue (e.g., localized cooling or heating of tissue), and in particular applying thermal therapy to the spinal canal, tissue disposed within the spinal canal, and/or nerve roots extending from the spinal canal. In some embodiments, tissue can be cooled or heated by implanting a malleable or deformable thermal device in proximity to the targeted tissue. The thermal device can be left in place following surgery to facilitate application of post-surgical thermal therapy. In some embodiments, the thermal device can be removed post-surgery in a minimally- or non-invasive manner. The thermal device can be connectionless or can include penetrable regions, pre-attached tubing, or detachable connectors to facilitate application of cooling or heating means to the device. Methods are disclosed for utilizing thermal devices and for carrying out various treatment regimens that involve cooling or heating tissue using such devices.

Certain exemplary embodiments will now be described to provide an overall understanding of the principles of the structure, function, manufacture, and use of the methods and devices disclosed herein. One or more examples of these embodiments are illustrated in the accompanying drawings. Those skilled in the art will understand that the methods and devices specifically described herein and illustrated in the accompanying drawings are non-limiting exemplary embodiments and that the scope of the present invention is defined solely by the claims. The features illustrated or described in connection with one exemplary embodiment can be combined with the features of other embodiments. Such modifications and variations are intended to be included within the scope of the present invention.

In the description that follows, reference is made primarily to treating tissue in and around the spinal canal, including the spinal cord, but it will be appreciated that the methods and devices disclosed herein can also be used to treat tissue in virtually any part of a human or animal body, including organs, joints (e.g., hips, knees, elbows, shoulders), the brain, the heart, etc. It will also be appreciated that the term "spinal tissue" as used herein can include the spinal cord itself, as well as nerves and nerve roots extending therefrom through spaces in the spinal column, together the "spinal neuraxis," as well as other portions of the central nervous system.

Furthermore, while methods and devices for cooling tissue are primarily disclosed herein, it will be appreciated that the same or similar methods and devices can be used to heat tissue, e.g., for the purpose of applying localized therapeutic hyperthermia.

In some embodiments, methods of applying thermal therapy involve "implanting" a thermal device in the patient. As used herein, "implanting" the thermal device refers to leaving at least a portion of the thermal device in the patient after the initial surgical phase of treatment is completed (e.g., by closing a tissue opening over the implanted device while tubing or connectors associated therewith extend through the closed incision). Implanting the thermal device facilitates delivery of postoperative thermal therapy, optionally for an extended time period or in multiple sessions over a prolonged period, which can provide unexpected benefits for the patient.

For example, peak edema typically does not subside until about three to five days after a spinal cord injury is sustained. With an implantable system, therapeutic hypothermia can be delivered throughout this period to minimize swelling-related damage to the patient's spinal cord. The ability to implant the thermal device also allows for the patient to be closed immediately following decompression, stabilization, or other surgery that may be performed in connection with implanting the device, yet still preserves the ability to apply thermal therapy for extended time periods. It is desirable to conclude the initial surgical phase of treatment as soon as possible so as to reduce the patient's exposure to possible infection, reduce the amount of time the patient must be under anesthesia, reduce the cost of the surgery by reducing the amount of time required of surgeons, operating staff, operating rooms, and other resources, improve hospital throughput by freeing up resources to treat other patients, and so forth.

The thermal device can be left implanted for any amount of time (e.g., at least about 1 hour, at least about 4 hours, at least about 12 hours, at least about 18 hours, at least about 24 hours, at least about 48 hours, at least about 72 hours, at least about 5 days, at least about 7 days, at least about 2 weeks, at least about 1 month, at least about 3 months, at least about 6 months, at least about 1 year, at least about 5 years, at least about 10 years, and/or permanently or indefinitely).

System

FIG. 1 illustrates an exemplary embodiment of a system 100 for applying thermal therapy. The system 100 generally includes a thermal device 102 and a source 104 configured to provide a cooling or heating means to the device 102. Delivery of the cooling or heating means can be regulated by a controller 106. The thermal device 102 can be an implantable container, pouch, balloon, pad, sac, etc. that can be positioned in proximity to tissue that is to be cooled or heated. The thermal device 102 can be placed in direct contact with the tissue to be cooled or heated, or can apply a cooling or heating effect to the tissue in an indirect manner, e.g., through intermediate tissue, implants, or other structures.

Exemplary tissue that can be cooled or heated using the thermal device 102 includes the spinous process, the vertebral body, the pedicles, the laminae, the spinal canal, the spinal canal contents (including the spinal cord), nerves (including those surrounding or extending to/from the spinal cord), vessels, and muscles. The spinal canal contents include, for example, epidural space, dura mater, subdural space, arachnoid space, subarachnoid space, intrathecal space, cerebral spinal fluid, pia mater, spinal arteries and veins, vasocorona, vertebral venous plexus, nerve roots, ligaments, and fatty tissue. It will be appreciated that there is symmetry as well as repetitive elements to a vertebra and referral to an element of the vertebra can be taken to mean any one of symmetric or multiple elements. For example, when referring to a pedicle, it can be intended to mean any one of the two, or both, pedicles of the vertebra.

Cooling/Heating Means and Source

The thermal device 102 can provide a cooling or heating effect using any of a number of different cooling or heating means or combinations thereof. For example, the cooling means can include the expansion of gas within the thermal device 102 or the circulating of a chilled fluid through the thermal device 102. The term "fluid," as used herein, refers to any flowable material or collection of materials, including liquids, gasses, and combinations thereof. In one embodiment, the thermal device 102 receives a compressed gas which by expansion acts as a coolant in the thermal device 102. The expansion of the gas causes the gas and the thermal device 102 around it to experience a rapid decrease in temperature. Typical gases for such an application include Nitrous Oxide and Carbon Dioxide, but it will be appreciated that there are a wide variety of gases that can be used, including gasses which, in compressed form, will be liquid.

In other embodiments, the thermal device 102 receives a chilled liquid as the cooling means which flows through cavities or channels of the thermal device, thereby decreasing the temperature of the thermal device. Typical chilled liquids include saline solutions, water, liquid nitrogen, and ethyl alcohol. It will be appreciated that any number of fluids can be used as the cooling means, and that there are advantages to using biologically safe fluids. In still other embodiments, the thermal device 102 can include a thermoelectric device, such as a Peltier device, which when a voltage or current is applied, at least a portion of the device experiences a reduction in temperature. The thermal device 102 can also house an endothermic chemical reaction which results in the reduction of temperature of the contents of the thermal device 102 and of the thermal device 102 itself. In other embodiments, the thermal device 102 is pre-chilled prior to a cooling procedure. It will be appreciated by those skilled in the art that there are a variety of means by which the thermal device 102 can be cooled.

The thermal source 104 can be external (e.g., extracorporeal), can be implanted in the patient, and/or can be formed integrally with the thermal device 102. In implementations in which the cooling means is an expanding gas, the thermal source 104 can be a tank of compressed gas which is released into the thermal device 102 through a cooling delivery conduit. Once the compressed gas is in the thermal device 102, it can be expanded through an expansion nozzle into an expansion chamber in the thermal device 102, causing a rapid decrease in temperature. Alternatively, or in addition, the thermal source 104 can include a compressor that compresses the gas. In some implementations, the delivery of the cooling means from the tank of compressed gas is regulated with the control unit 106 to limit the amount of gas and the pressure at which it enters the thermal device 102 via the cooling delivery conduit. The control unit 106 can be an adjustable valve on the tank, which can be manually controlled, mechanically controlled, or automatically controlled by a computing device. In implementations in which the thermal source 104 includes a compressor, the control unit 106 can control the degree to which the compressor compresses the gas, or the pressure of the gas presented down the conduit. The regulation of the release of the gas can be managed manually or automatically, in either case, based on established protocols, conditions of the patient, and/or detectable physiological characteristics of the patient or characteristics of the thermal device.

An additional conduit can also be provided to exhaust expanded gas from the expansion chamber of the thermal device 102. The exhaust conduit can exhaust the gas into the atmosphere, to a collection tank, or to a compressor which in turn re-compresses the gas for reuse. As discussed further below, the delivery conduit and the exhaust conduit can be generally circular in cross-section, and can be formed from any of a variety of medical-grade tubing materials known in the art. The conduits can be flexible or rigid, or can include rigid portions and flexible portions.

In implementations in which the cooling means is a chilled fluid, the thermal source 104 can be or can include a chiller or other apparatus for cooling and pumping fluid, and the cooling delivery conduit can be a tube for delivering the chilled fluid to the thermal device 102. In this case, the exhaust conduit can be used to return or exhaust the chilled fluid from the thermal device 102 back to the thermal source 104, to a collection tank, or to a drain. In such an implementation, the control unit 106 can control the volume rate of chilled fluid flow, the pressure of the chilled fluid delivery lines, and/or the temperature of the chilled fluid. It will be appreciated that components of the fluid delivery and circulation system can be positioned on the exhaust side of the system rather than the source side (e.g., a pumping mechanism that pulls the chilled fluid through the device 102, the delivery conduit, and the exhaust conduit rather than pushing it through).

In implementations in which the cooling means is a Peltier device embedded in the thermal device 102, the thermal source 104 can include a power supply that powers the Peltier device, and the cooling delivery conduit can include electrical lines that supply electrical current from the power supply to the Peltier device. The delivery and exhaust conduits can also be used to remove heat generated by the Peltier device from the thermal device 102.

Delivery of the cooling means can be regulated to achieve a predetermined cooling effect, such as a specific temperature at a specific location. Delivery of the cooling means can also be regulated such that a specific volume of the cooling means is delivered, for example in cases where the cooling means includes a chilled liquid or expandable gas. Delivery of the cooling means can also be regulated based on changes or lack of changes in physiological characteristics. For example, the regulation of the cooling means, and thus the intensity of cooling, can be determined by quantitative and qualitative sensory or motor-evoked potential (SEP, MEP) observations. In this example, the cooling means is provided at a certain level until the patient's SEP/MEP results begin to degrade, improve, or otherwise change, at which point the regulation of the cooling means can begin to reduce or increase the delivery of the cooling means.

It will be appreciated that any number of physiological characteristics can be used to regulate the intensity of the cooling means, including but not limited to: blood pressure, target-tissue temperature, specific tissue temperature (proximate to target tissue), rectal body temperature, venous blood temperature near or exiting target tissue, pulmonary conditions, cardiac conditions, sensory evoked potentials (SEPs, including somatosensory evoked potentials), motor-evoked potentials (MEPs), intrathecal pressure, perfusion pressure, levels of blood oxygen & glucose, ATP concentrations, and effectors of excitotoxicity, vasogenic edema, apoptosis, inflammation, and enzymatic responses. A real-time qualitative or quantitative determination can be made based on any of the listed physiological characteristics as to how the cooling means should be regulated.

One or more sensors can also be included in the thermal device 102 and/or implanted in or around the patient. The sensor can be a temperature sensor embedded in or on the thermal device 102 to sense the temperature the device exhibits, where this sensed temperature can then be used to control the delivery of the cooling means to the thermal device 102. The sensor can be connected to the control unit 106 via one or more sensor wires to provide a feedback loop of information to help determine how much cooling means and/or what temperature cooling means to deliver to the thermal device 102. Alternatively, or in addition, the sensor can be connected via sensor wires to a display, meter, dial, or other indicator providing some form of output data from the sensor that can allow one to manually regulate the delivery of the cooling means. The sensor can also be connectable wirelessly and a wireless link can be used instead of the sensor wires.

In one implementation, a first sensor is embedded into the thermal device 102 and provides temperature data of the thermal device 102 and a second sensor is implanted in the intrathecal space of the spinal canal to measure temperature of cerebral spinal fluid. This temperature data can be used to either manually or automatically regulate the delivery of the cooling means.

It will be appreciated that more than one sensor, more than one sensor type, and more than one sensor placement location can be used simultaneously and that the data gathered from the multiple sensors can be used independently or in combination to determine how the delivery of the cooling means is regulated. Exemplary sensors that can be used include temperature sensors (e.g., thermistors or thermocouples), pressure sensors, chemical sensors, electrical sensors, magnetic sensors, and optical sensors. Other types of sensing, such as remote sensing, can be used that do not require the sensor itself to be placed within the patient—ultrasound, including Doppler measurements, and functional MRI, all can be used to sense physiological characteristics that can be used to control or regulate the delivery of the cooling means. The information measured by a sensor or sensors can be used to continually adjust the regulation of the delivery of the cooling means in real time or almost real time. Alternatively, or in addition, the sensed information can be used for safety monitoring. The advantages of using a sensor or sensors, along with sensor wires or other communication means, will be appreciated though their use may not be necessary.

Thermal Devices

Figure 2:
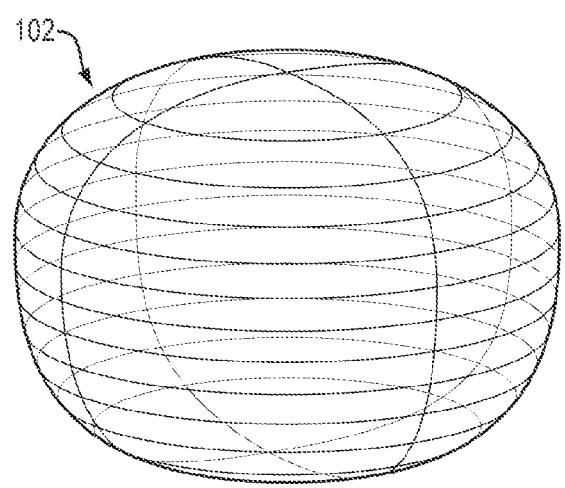
FIG. 2 is a perspective view of an ellipsoid thermal device.
Figure 3:
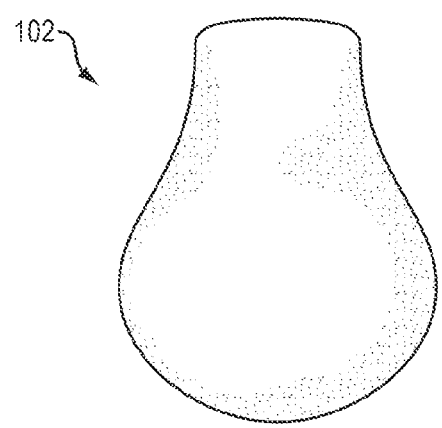
FIG. 3 is a perspective view of a pear-shaped thermal device.
Figure 4:
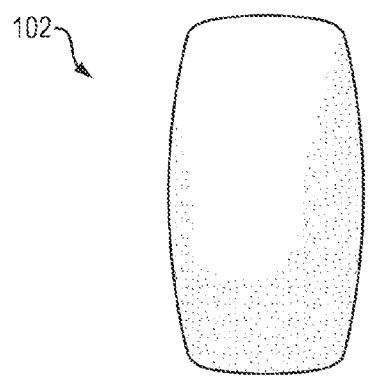
FIG. 4 is a perspective view of a cylindrical thermal device.
Figure 5:
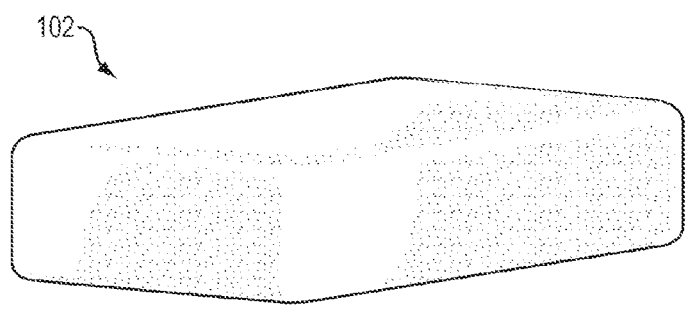
FIG. 5 is a perspective view of a box-shaped thermal device.
Figure 6:
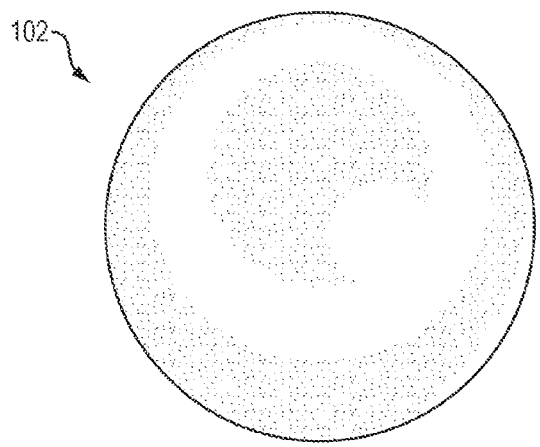
FIG. 6 is a perspective view of a spherical thermal device.
Figure 7:
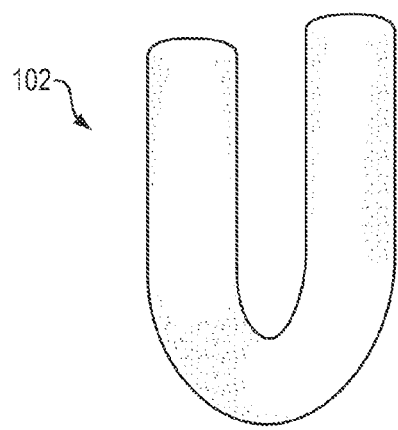
FIG. 7 is a perspective view of a U-shaped thermal device.
Figure 8:
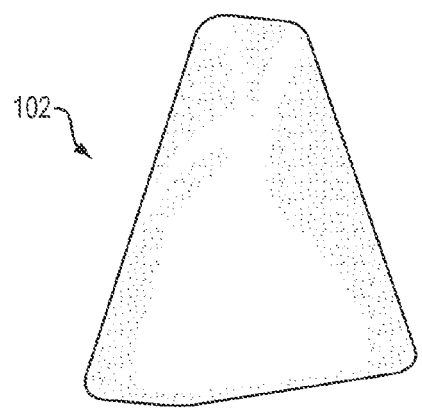
FIG. 8 is a perspective view of a triangular thermal device.
Figure 9:
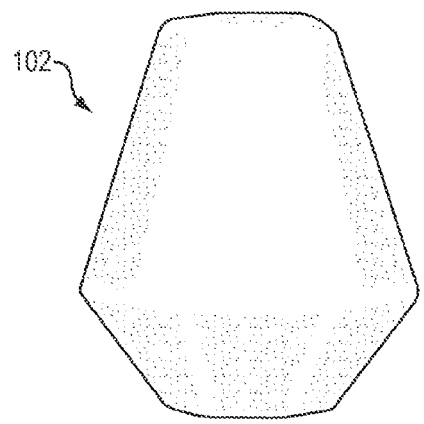
FIG. 9 is a perspective view of a faceted pear-shaped thermal device.
Figure 10:
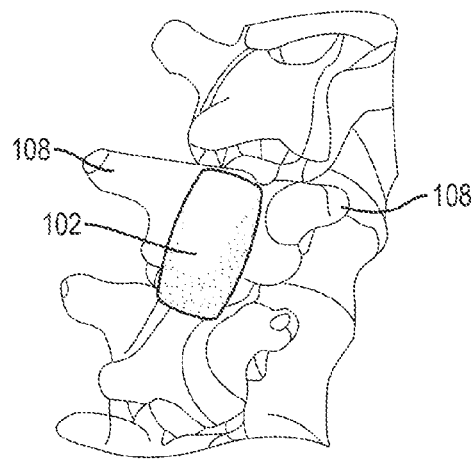
FIG. 10 is a perspective view of a rectangular thermal device positioned over a patient's dura.
Figure 11:
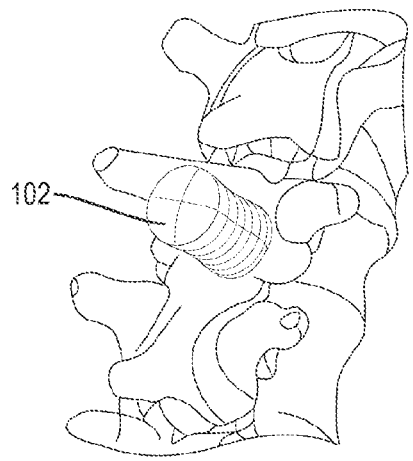
FIG. 11 is a perspective view of a cylindrical thermal device positioned over a patient's dura.
Figure 12:
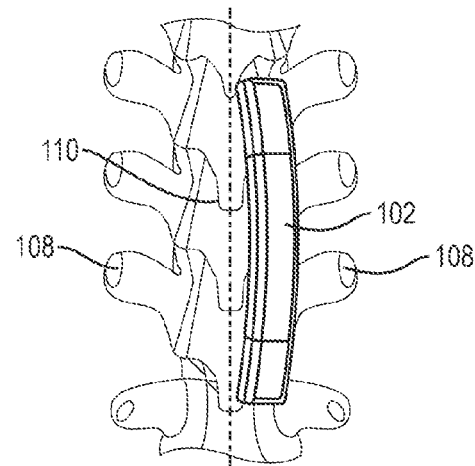
FIG. 12 is a perspective view of a rectangular thermal device positioned over multiple levels of a patient's spinal column.
Figure 13:
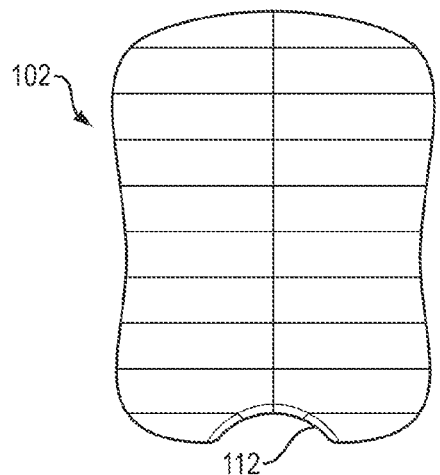
FIG. 13 is a profile view of a thermal device with a recess for receiving a portion of a patient's anatomy.

An exemplary thermal device 102 is shown in FIG. 2. As shown, the device 102 is generally in the form pad that can be positioned adjacent to a target region of a patient to apply thermal therapy thereto. The pad 102 can have an ellipsoid or spheroid shape as shown in FIG. 2 or any of a variety of other shapes. For example, the pad 102 can have a pear shape as shown in FIG. 3, a cylindrical shape as shown in FIG. 4, a box shape as shown in FIG. 5, a spherical shape as shown in FIG. 6, a U-shape as shown in FIG. 7, a triangular shape as shown in FIG. 8, a faceted pear shape as shown in FIG. 9, etc. In some embodiments, the pad 102 can be sized and shaped based on the anatomy that is targeted for thermal therapy. For example, as shown in FIG. 10, the pad 102 can have a substantially flat, rectangular shape with rounded corners and convex edges and can be sized to fit between the transverse processes 108 and cover the exposed dura or spinal cord after a single-level laminectomy. By way of further example, as shown in FIG. 11, the pad 102 can have a substantially cylindrical shape and can be sized to fit through a cylindrical tissue pathway in order to position a distal end surface of the pad over the dura or spinal cord. The pad 102 can be positioned in contact with or in close proximity to the dura surrounding the spinal cord. As shown in FIG. 12, the pad 102 can have an elongate, substantially flat, and rectangular shape with rounded corners and can be sized to extend across multiple levels of the spinal column. The pad 102 can be placed over the intact lamina between the transverse and spinous processes 108, 110 as shown, or can be placed directly over the exposed dura or spinal cord after a multi-level laminectomy. The pad 102 can also be placed over one or more spinal implants, such that the pad 102 covers the implants and/or is in direct contact with or in close proximity to the implants. As shown in FIG. 13, the pad 102 can include a recess or hemi-cylindrical depression 112 in its distal end surface sized to receive at least a portion of the patient's spinal cord. It will be appreciated that the pad 102 can have virtually any size or shape and that the size and shape can be selected based on various factors such as the anatomical location of the target site, the age, weight, species, or sex of the patient, the nature of the injury or condition suffered by the patient, and the types of procedures to be performed in conjunction with thermal therapy (e.g., laminectomy, vertebral fusion, and the like).

The thermal device 102 can be a homogenous block of material (e.g., a gel or a solid), or can include an outer membrane that defines an inner reservoir. The inner reservoir can be filled with any of a variety of materials or media, including gels or liquids such as saline. The membrane and/or the reservoir media can be bio-absorbable. The reservoir media, or any fluid that is supplied to or circulated through the reservoir, can include a radiographic or magnetic tracer to allow detection of media migration out of the device using known imaging systems.

The device 102 can be rigid or can be resiliently or non-resiliently malleable or deformable such that the device can be conformed to the anatomical structures to which it is applied. In particular, the device 102 can include a malleable membrane configured to form a substantial negative of the anatomy against which it is placed to maximize the contact surface area between the membrane and the anatomy.

The device 102 can be formed from any of a variety of materials. Exemplary materials include Silicone, Polyethylene terephthalate (PET), Nylon, Polyethylene (PE), Polyurethane, Polyvinyl chloride (PVC), Latex, Titanium, Steel, Gold, Cobalt Chrome, and combinations thereof. The device 102 can have any of a variety of dimensions. The device 102 can have dimensions of 10 mm diameter×5 mm tall. The device 102 can have dimensions of 20 mm diameter×20 mm tall. The device 102 can have dimensions of 40 mm diameter×40 mm tall. The device 102 can have dimensions of 40 mm diameter×70 mm tall. The device 102 can have dimensions of 10 mm long×10 mm wide×3 mm tall. The device 102 can have dimensions of 20 mm long×20 mm wide×3 mm tall. The device 102 can have dimensions of 30 mm long×10 mm wide×5 mm tall. The device 102 can have dimensions of 60 mm long×15 mm wide×6 mm tall. The device 102 can have dimensions of 100 mm long×30 mm wide×15 mm tall. The device 102 can have dimensions of 300 mm long×60 mm wide×30 mm tall. The device 102 can occupy a volume of at least about 0.3 milliliters, at least about 0.4 milliliters, at least about 1.2 milliliters, at least about 1.5 milliliters, at least about 5.4 milliliters, at least about 6.3 milliliters, at least about 45 milliliters, at least about 50.3 milliliters, at least about 88 milliliters, or at least about 540 milliliters.

The device 102 can be at least partially radiopaque to facilitate visualization using fluoroscopy or other radiation-based imaging techniques. For example, the device 102 can include a radiopaque membrane or can be filled or impregnated with radiopaque particles.

The device 102 can include one or more embedded sensors, including any of the sensors described above, as well as passive RFID temperature sensors which can be used to monitor the temperature of the device. At least a portion of the device 102 can allow transmission of infrared wavelengths to detect the temperature of the device using external infrared measurement devices. For example, the proximal-facing surface of the device 102, or the entire device, can be formed from a material that permits infrared radiation to pass. Various other external, non-contact ways of measuring temperature can also be employed.

In some embodiments, as shown for example in FIG. 2, the device 102 has no external connections and instead serves as a passive heat sink device. The device 102 can be pre-chilled (e.g., in an ice bath, refrigerated chamber, etc.) before being placed or implanted in the patient. Alternatively, or in addition, the device 102 can be cooled while inside the body by an active thermal device disposed adjacent thereto (e.g., disposed outside the body).

It will be appreciated, however, that the device 102 can also include one or more external connections, such as electrical leads for sensors or a Peltier cooling device, or fluid conduits for addition, extraction, or circulation of fluid.

Figure 14:
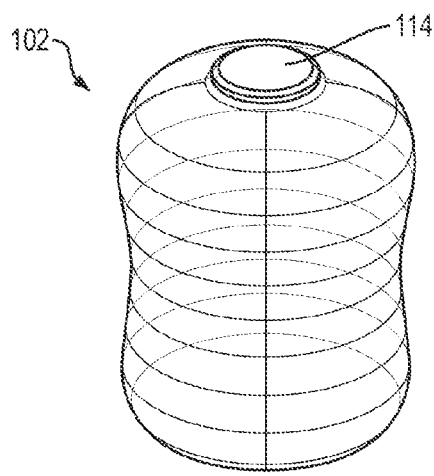
FIG. 14 is a perspective view of a cylindrical thermal device having a circular penetrable region.
Figure 15:
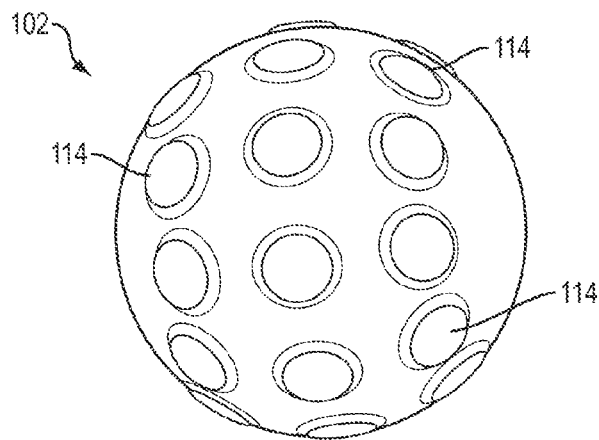
FIG. 15 is a perspective view of a spherical thermal device having a plurality of circular penetrable regions.
Figure 16:
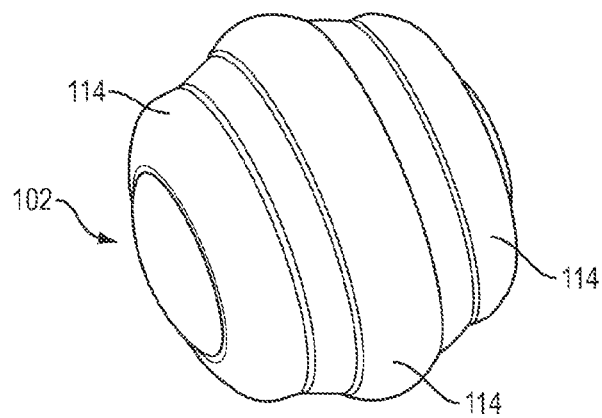
FIG. 16 is a perspective view of a spherical thermal device having a plurality of ring-shaped penetrable regions.
Figure 17:
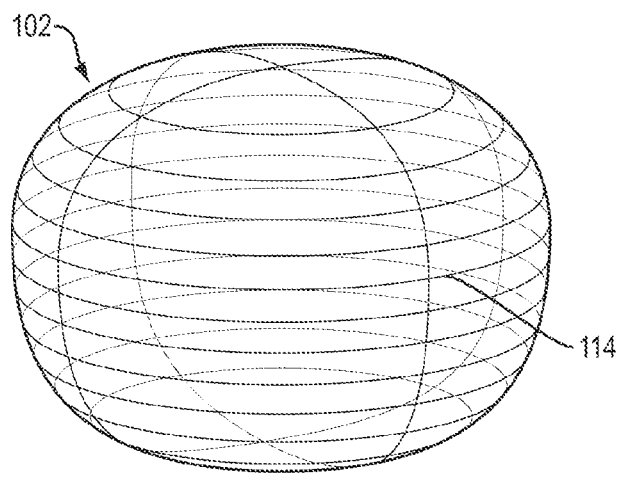
FIG. 17 is a perspective view of an ellipsoid thermal device in which the entire exterior surface is a penetrable region.

For example, the device 102 can include one or more penetrable areas through which a connector can be inserted to facilitate thermal regulation of the device. FIG. 14 illustrates an exemplary cylindrical thermal device 102 that includes a circular penetrable region 114 formed in its proximal-facing end surface. FIG. 15 illustrates an exemplary spherical thermal device 102 that includes a plurality of circular penetrable regions 114 formed in ring patterns about the outer surface of the device. FIG. 16 illustrates an exemplary spherical thermal device 102 that includes a plurality of ring-shaped penetrable regions 114. FIG. 17 illustrates an exemplary ellipsoid or spheroid thermal device 102 in which the entire exterior surface of the device is a penetrable region 114.

The penetrable regions can be formed from a different material than that used to form the remaining portions of device's outer membrane. The penetrable regions can also be formed form the same or similar material, but with a lower stiffness or durometer. In some embodiments, the penetrable regions are formed from an elastomer such as silicone. The penetrable regions can be self-sealing, such that they are configured to maintain a fluid-tight seal around a connector inserted therethrough and/or after a connector is removed therefrom. The area immediately surrounding the penetrable regions can be reinforced to prevent tearing during insertion of a connector through the penetrable area.

Figure 18:
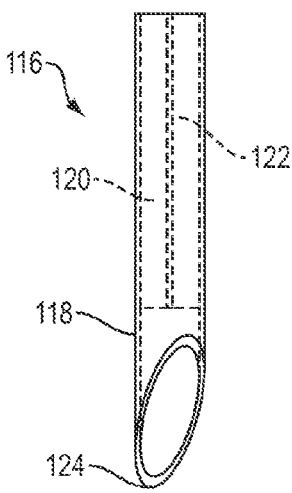
FIG. 18 is a profile view of a connector for penetrating a penetrable region of a thermal device.
Figure 19:
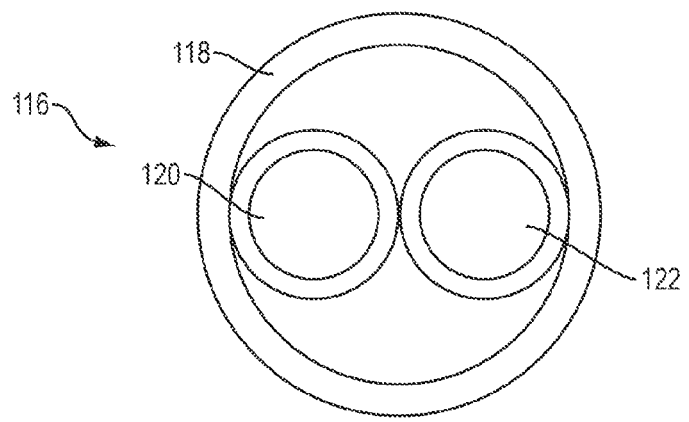
FIG. 19 is an end view of the connector of FIG. 18.
Figure 20:
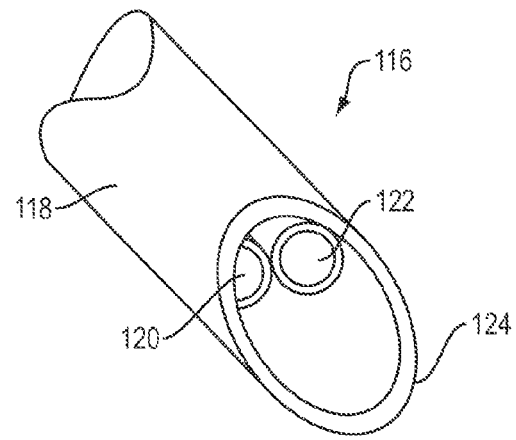
FIG. 20 is a perspective view of the connector of FIG. 18.
Figure 21:
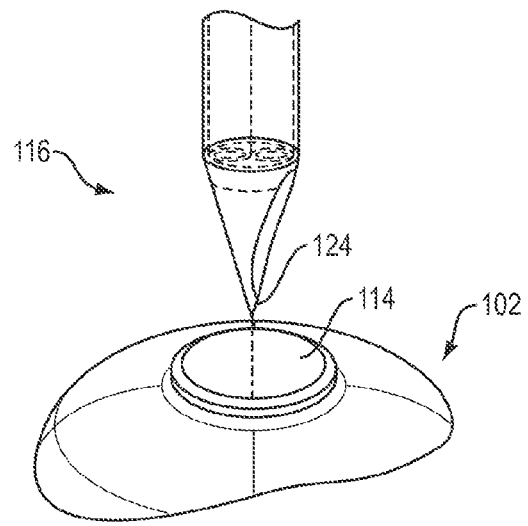
FIG. 21 is a profile view of a connector for penetrating a penetrable region of a thermal device.
Figure 22:
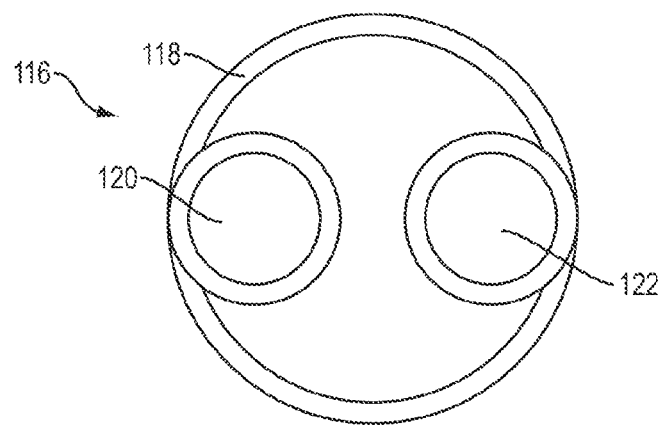
FIG. 22 is an end view of the connector of FIG. 21.
Figure 23:
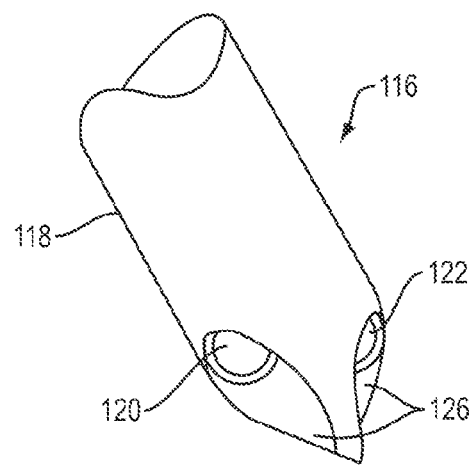
FIG. 23 is a perspective view of the connector of FIG. 21.
Figure 24:
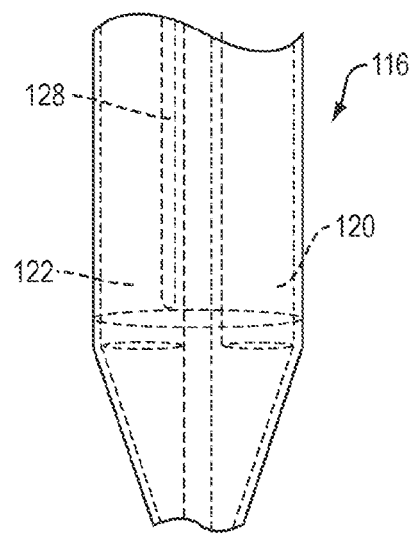
FIG. 24 is a profile view of a connector with an embedded sensor.

FIGS. 18-20 illustrate an exemplary connector 116 that can be used with penetrable thermal devices. As shown, the connector 116 generally includes an elongate cylindrical body 118 having one or more fluid lumens (e.g., a fluid inlet conduit 120 and a fluid outlet conduit 122) disposed therein. The connector 116 can be a solid cylindrical body in which the fluid lumens 120, 122 are defined. Alternatively, the body of the connector 116 can be a tubular sheath disposed around one or more independent fluid lumens. The distal tip 124 of the connector can be shaped to facilitate insertion of at least a portion of the connector through a penetrable area of the thermal device 102. In the embodiment shown in FIGS. 18-20, the distal tip of the connector has a slash-cut or angled shape to define a sharpened tip. FIGS. 21-23 illustrate a connector 116 in which the distal tip 124 is conically-shaped. Cylindrical bores 126 formed in the conical tip 124 form fluid pathways between the fluid lumens 120, 122 of the connector body and the exterior of the tip. As shown in FIG. 24, the connector 116 can include an embedded temperature probe or other sensor 128 for detecting various attributes of the environment in and around the distal tip of the connector 116. Exemplary temperature sensors include a simple wire thermocouple. Various other sensors can also be included, such as pressure, pH, or any of the other sensor types disclosed herein. In some embodiments, the sensor 128 can be disposed within the fluid outlet conduit 122 or in close proximity to the fluid outlet conduit, as this can be the most accurate location to measure certain parameters such as temperature. The connector 116 can be rigid or flexible, or can include one or more rigid portions and one or more flexible portions.

In use, the connector 116 can be inserted through a penetrable area 114 of the thermal device 102 to form a pathway between the thermal device and the thermal source 104 through which cooling or heating media can be conveyed.

Other connection mechanisms can be used instead of, or in addition to, the penetrable regions described above. For example, the thermal device 102 can include integral or pre-attached tubing, or a port to which a connector can be selectively coupled and decoupled.

Figure 25:
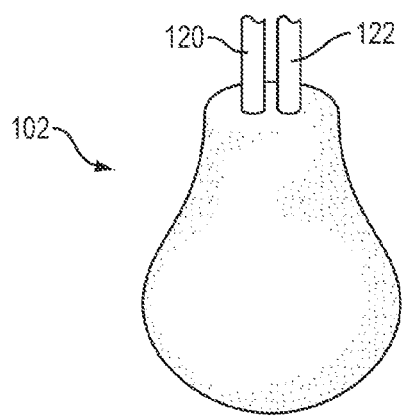
FIG. 25 is a perspective view of a thermal device with pre-attached tubing.

FIG. 25 illustrates an exemplary thermal device 102 having pre-attached or integrally-formed inlet and outlet conduits 120, 122. The conduits 120, 122 can include embedded sensors, such as temperature sensors. The conduits 120, 122 can also include a frangible seam portion to allow the conduits to be broken off or otherwise separated from the thermal device 102. In some embodiments, at least a portion of the conduits 120, 122 can be formed from a bioabsorbable material such that the conduits are naturally separated from the thermal device 102 with time as they are absorbed by the body.

Figure 26:
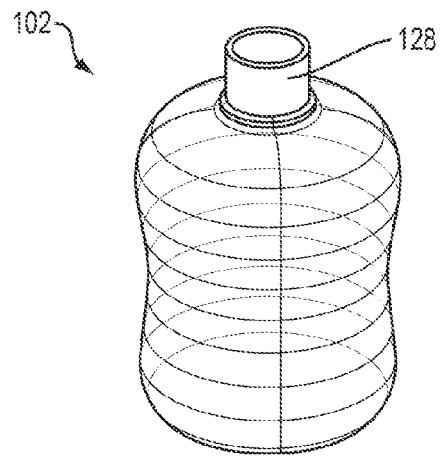
FIG. 26 is a perspective view of a thermal device with a port that can be selectively coupled to a connector.
Figure 27:
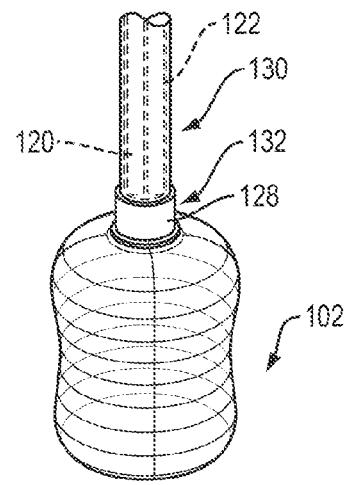
FIG. 27 is a perspective view of the thermal device of FIG. 26 with a connector coupled to the port.
Figure 28:
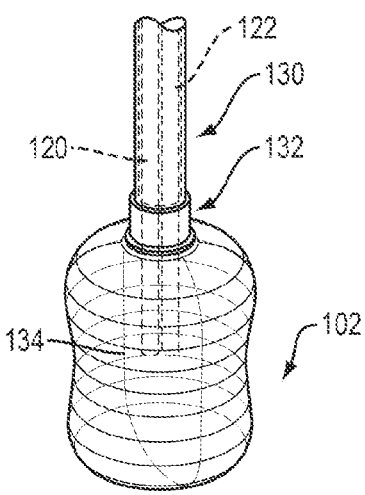
FIG. 28 is a perspective view of a thermal device with a connector that extends into the interior of the device.

FIG. 26 illustrates an exemplary thermal device 102 having a port 128 to which a connector can be selectively coupled or decoupled. As shown in FIG. 27, the connector 130 can include inlet and outlet conduits 120, 122 and a mating feature 132 to facilitate attachment of the connector to the port 128 of the thermal device 102. Any of a variety of mating features can be used for this purpose, including interference connections, threaded connections, snap-fit connections, detents, latches, pins, compression fittings, and the like. In some embodiments, the mating features can provide a positive mechanical interlocking connection. The connector 130 can also include various mechanisms for disengaging the connector from the thermal device 102. For example, the connector can include a rip-cord that, when pulled from outside the patient, breaks a connection between the connector and the thermal device. The connector can also include any of a variety of embedded sensors, including one or more temperature sensors. The port 128 can be self-sealing such that a fluid-tight seal is formed when the connector 130 is disconnected from the thermal device 102. For example, the port 128 can include a resilient flap that is deflected out of position when a connector 130 is coupled to the port to allow fluid flow into and out of the device. When the connector 130 is removed, the biased flap can automatically return to its closed position, sealing off the port 128. As shown in FIG. 28, the mating feature 132 of the connector 130 can be set back from the distal end of the connector such that the connector extends partially into the interior of the thermal device 102. As also shown in FIG. 28, the thermal device 102 can include one or more internal baffles or walls 134 to direct or guide fluid flow through the device. For example, the thermal device 102 can include a center baffle 134 aligned with the connector interface such that, when the connector 130 is mated to the thermal device, the fluid inlet conduit 120 is aligned with a first side of the baffle and the fluid outlet conduit 122 is aligned with a second, opposite side of the baffle.

Figure 29:
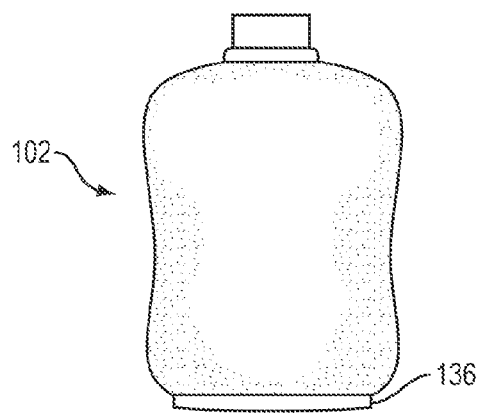
FIG. 29 is a profile view of a thermal device with a heat transfer element.

FIG. 29 illustrates a thermal device 102 that includes a heat transfer element 136. In the illustrated embodiment, the heat transfer element is disposed across a distal end surface of the thermal device, though it will be appreciated that any portion of the device can include a heat transfer element. The heat transfer element can be configured to enhance the transfer of thermal energy between the thermal device and the abutting anatomy. The heat transfer element can be formed from a material having a high thermal conductivity, such as biocompatible metals or ceramics. In use, the distal end surface of the device, and thus the heat transfer element, can be positioned against the patient's spinal cord, dura, or other treatment region. The heat transfer element can be shaped or contoured to match the target anatomy. For example, the heat transfer element can include a hemi-cylindrical groove or recess sized to receive a portion of the spinal cord.

Figure 30:
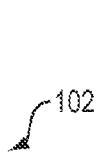
FIG. 30 is a profile view of a thermal device in a collapsed configuration.
Figure 31:
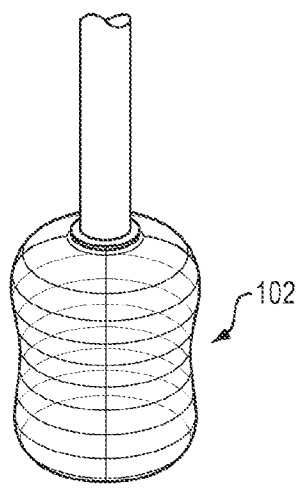
FIG. 31 is a profile view of a thermal device in an expanded configuration.

As shown in FIGS. 30-31, the thermal device 102 can be partially or completely collapsible to facilitate insertion, removal, or adjustment of the thermal device. For example, the thermal device 120 can be inserted into a target site within a patient in a first, collapsed configuration (shown in FIG. 30) and then fluid can be supplied to the device to transition the device to a second, expanded configuration (shown in FIG. 31). When removal of the thermal device is desired, or at any other appropriate time, the device can be partially or completely evacuated of fluid to cause or allow the device to collapse back to the first configuration. The device can be configured to collapse radially as shown, such that a diameter of the collapsed device is less than that of the device when in its expanded state. Alternatively, or in addition, the device can be configured to collapse into a flat disc, such that a height of the collapsed device is less than that of the device when in its expanded state.

The thermal device 102 can also be rolled and unrolled to transition the device between collapsed and expanded configurations, respectively. For example, the device can include a resilient wireframe disposed or embedded therein that biases the device towards a rolled configuration in which at least one dimension of the device is reduced. Upon application of cooling fluid to the device, the bias of the wireframe is overcome and the device transitions to the expanded configuration. When removal of the device is desired, or at any other desired time, fluid can be extracted from the device to allow the bias of the wireframe to return the device to the collapsed configuration.

Figure 32:
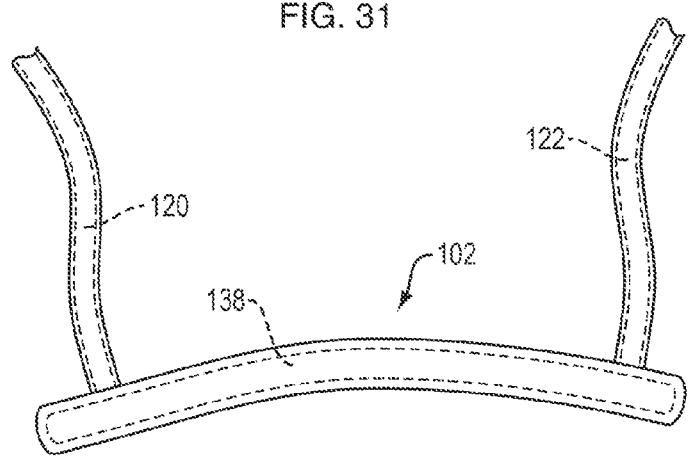
FIG. 32 is a profile view of a thermal device having multiple connections.
Figure 33:
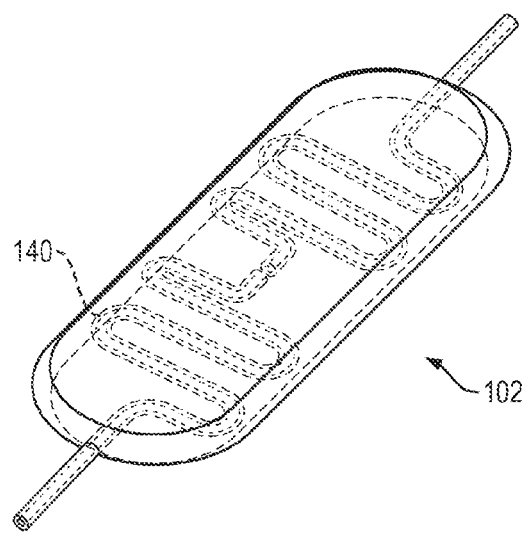
FIG. 33 is a perspective view of a thermal device with an internal fluid pathway.

The thermal device can include a single connection or multiple connections. For example, as shown in FIG. 32, the device 102 can include separate connections for delivering cooling means and removing cooling means. In the illustrated embodiment, the thermal device is a substantially rectangular pad 102 with a fluid inlet conduit 120 at a first end of the device and a fluid outlet conduit 122 at a second, opposite end of the device. The inlet and outlet conduits can be placed in fluid communication with the device via connectors inserted through penetrable regions, pre-attached or integral conduits, and/or connectors configured to be selectively coupled and decoupled from one or more ports of the device. The device 102 can include an inner reservoir 138 that occupies substantially the entire interior of the device, as shown in FIG. 32. Alternatively, the device 102 can include one or more defined fluid pathways extending therethrough. FIG. 33 illustrates an exemplary fluid pathway 140 that is coiled or snaked through the device to ensure that fluid flows through a significant portion of the device. The fluid pathway can include one or more branches, with paths arranged in any direction or pattern. The fluid paths can be contained within the body of the device, or can be attached or coupled to an exterior surface of the device.

Figure 34:
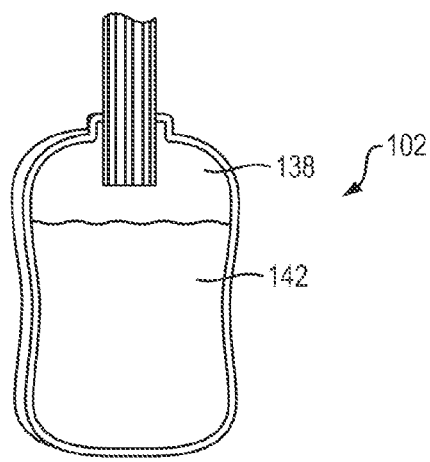
FIG. 34 is a cross-sectional perspective view of a cylindrical thermal device with a gel-filled inner reservoir.
Figure 35:
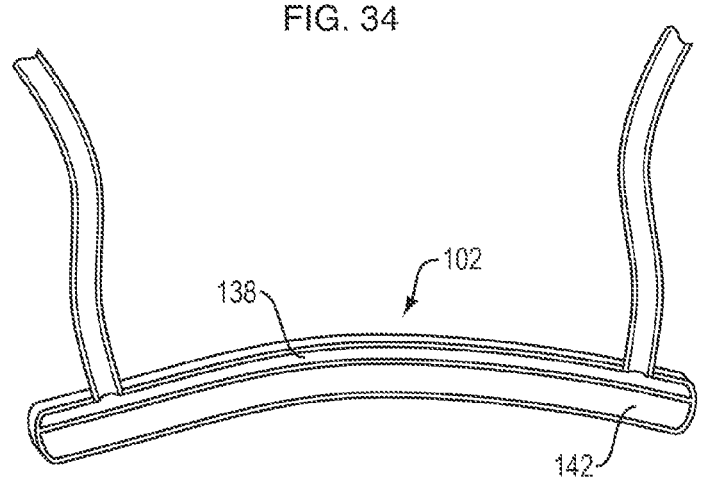
FIG. 35 is a cross-sectional perspective view of a rectangular thermal device with a gel-filled inner reservoir.

As shown in FIGS. 34 and 35, in embodiments in which the device 102 includes an inner reservoir 138, the reservoir can be filled or at least partially filled with a gel or other substrate 142. In some embodiments, the cooling fluid can be circulated through the reservoir, and can flow through the gel 142 and/or over or across the gel. The gel can be biocompatible and/or bioabsorbable. Exemplary gel materials include polymers such as poly-L lactic acid (PLLA), polyglycolic acid (PGA), polylactic acid (PLA), and combinations thereof. The gel can act as an internal heat sink and can allow the device to have a defined or semi-rigid shape before fluid supply is initiated. In other words, the device can have a self-supported shape or dough-like quality to it while implanting and before fluid flow begins.

Figure 36:
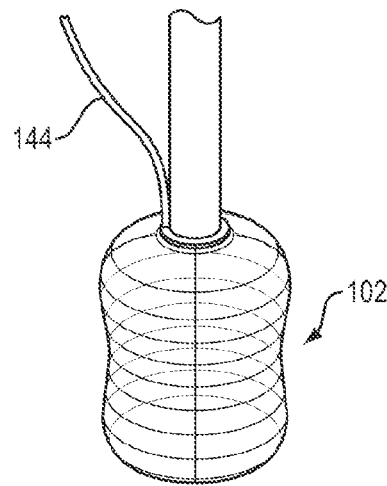
FIG. 36 is a perspective view of a thermal device with a tether.

The thermal device 102 can also include one or more tethers to facilitate positioning of the device, removal of the device from the surgical site, or separation of a connector from the thermal device. The device can include a plurality of tethers, which can be coupled to various points on the device. For example, the device can include first and second tethers attached to opposed sides of the device to allow the device to be shifted laterally or longitudinally or to be rotated within the surgical site. As shown in FIG. 36, the tether 144 can be a small gauge cord, wire, suture, or tube and can extend proximally from the thermal device 102 (e.g., to a point outside of the patient when the thermal device is implanted or positioned in the patient). The pre-attached tubing or selectively attachable connectors described above can be used as tethers. In other words, the tubing or connectors can be conceptualized as tethers having embedded or integrated tubing to facilitate media flow into and out of the thermal device. The tether can also be embedded in or tied up with the tubing that supplies fluid to the device, and the tether can be used to detach the tubing like a rip cord or grenade pin. Any of the techniques described above for separating tubing or connectors from the thermal device (e.g., bio-absorption, frangible portions, etc.) can be applied to make the tether removable from the device. The tether can include one or more embedded sensors, including any of the sensors described above.

Figure 37:
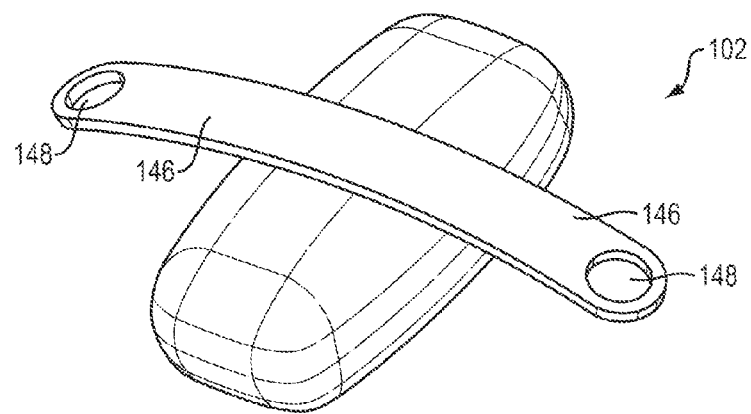
FIG. 37 is a perspective view of a thermal device that is attachable to a patient's anatomy or to other devices or implants.
Figure 38:
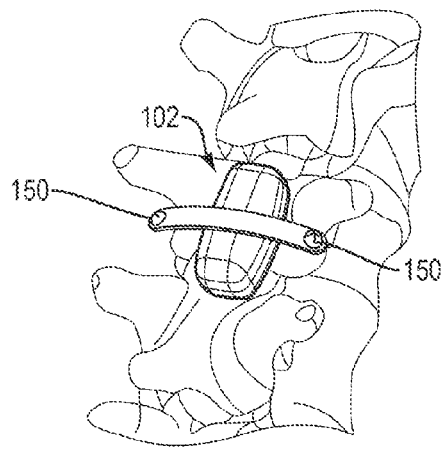
FIG. 38 is a perspective view of the thermal device of FIG. 37 coupled to a patient's vertebra by first and second bone fasteners.
Figure 39:
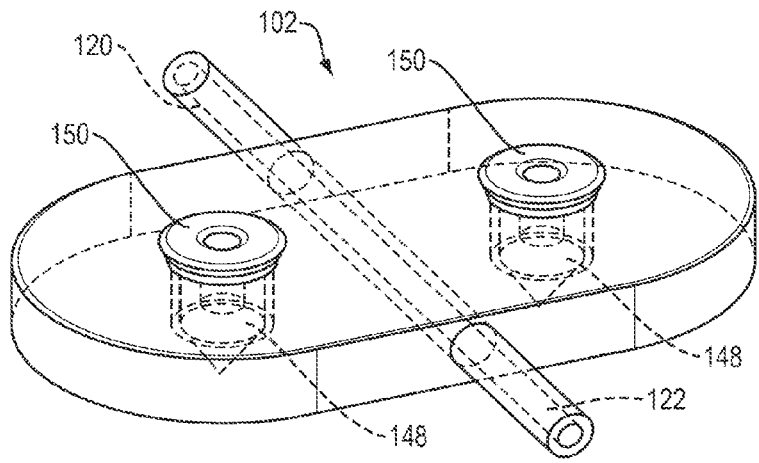
FIG. 39 is a perspective view of a thermal device having through holes for receiving fasteners.
Figure 40:
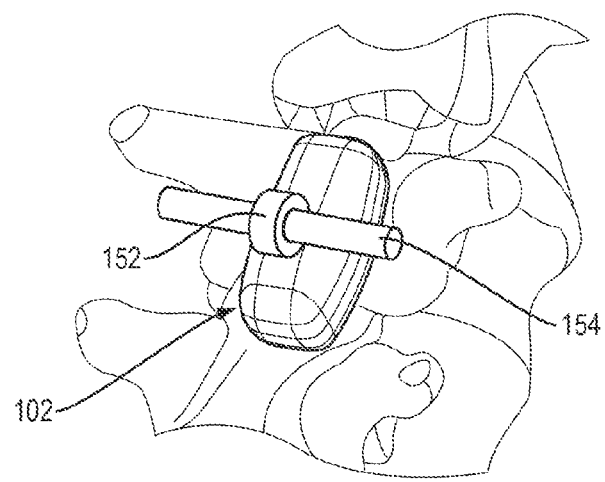
FIG. 40 is a perspective view of a thermal device positioned over a patient's dura and attached to a spinal cross-connector.
Figure 41:
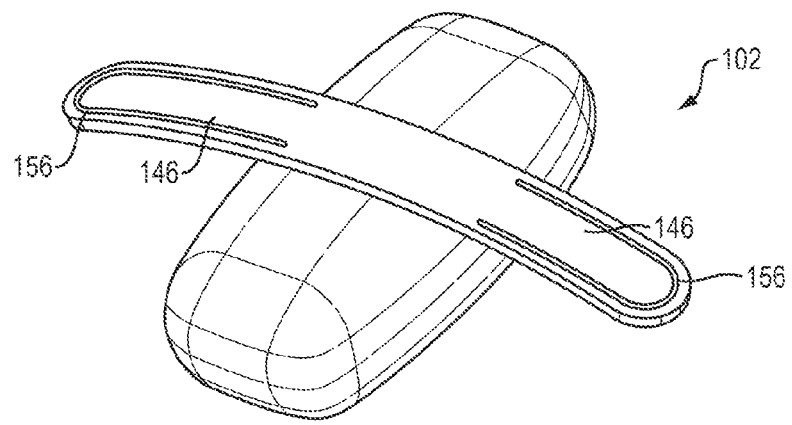
FIG. 41 is a perspective view of a thermal device with embedded wireframe hooks.

The thermal device can also include one or more attachment features for coupling the thermal device to the patient's anatomy or to one or more ancillary devices (e.g., implants, stabilization hardware, and so forth). For example, as shown in FIG. 37, the device 102 can include lateral wings 146 with openings 148 formed therein through which a fastener can be applied. As shown in FIG. 38, the wings 146 can be attached to bony tissue of the patient (e.g., vertebral bone) using bone screws, pins, staples, hooks, spikes, or other fasteners 150. The wings 146 can also be coupled to a spinal implant, for example by inserting at least a portion of the implant through the opening 148. By way of further example, as shown in FIG. 39, the device 102 can include through holes 148 formed in the body of the device though which fasteners 150 can be applied to attach the device to the patient's anatomy or one or more ancillary devices. As yet another example, as shown in FIG. 40, the device 102 can include hooks, loops, or other connectors 152 for coupling the device to ancillary devices such as spinal cross-connector 154. While a cross-connector is shown, it will be appreciated that the hooks or loops can be sized, positioned, or otherwise configured to attach the device to any of a variety of devices, including spacers, bone screws, fixation rods, and other hardware. As shown in FIG. 41, the device 102 can include wings or tabs 146 with a malleable wireframe 156 disposed therein. The wireframe can be bent to hook or clamp the device to patient anatomy or to an implant or other device. Any of a variety of other techniques can be used to secure or couple the device, including standalone clamps, sutures, etc.

By coupling the device to the patient anatomy or other implanted devices, the device can be maintained in a desired position or orientation within the patient for extended periods of time, including well after a surgical procedure for implanting the device is completed.

Figure 42:
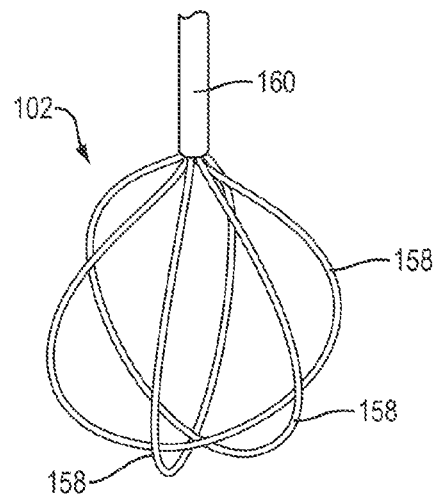
FIG. 42 is a perspective view of a thermal device having a plurality of exposed loops of tubing.
Figure 43:
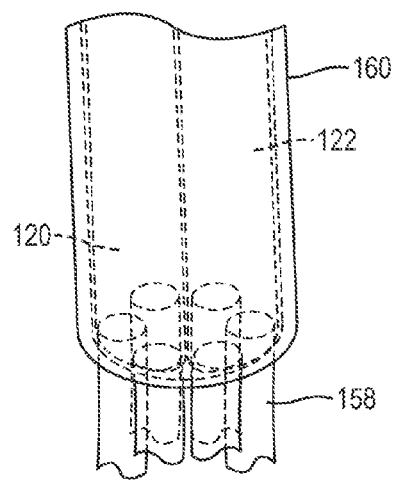
FIG. 43 is a perspective view of a portion of the thermal device of FIG. 42.
Figure 44:
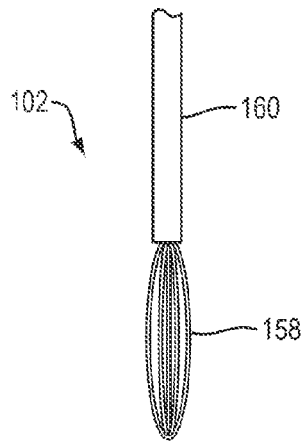
FIG. 44 is a profile view of the thermal device of FIG. 42 in an elongated insertion or removal configuration.
Figure 45:
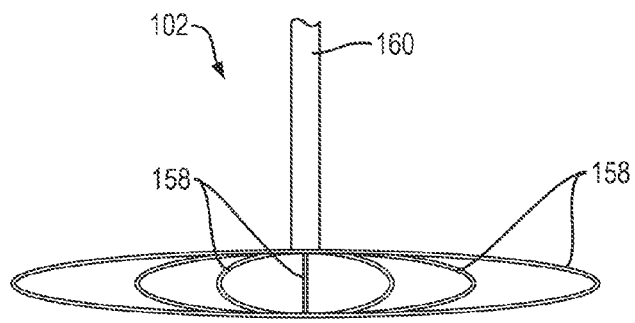
FIG. 45 is a profile view of the thermal device of FIG. 42 in a flattened therapeutic delivery configuration.

As shown in FIGS. 42-43, the thermal device 102 can include a plurality of flexible or semi-flexible exposed tubular loops 158 coupled to a connector 160. For example, a fluid inlet conduit 120 extending through the connector 160 can branch into a plurality of tubes 158 which extend distally outside of the connector. The plurality of tubes 158 loop back and couple to a fluid outlet conduit 122 extending through the connector 160. In some embodiments, the plurality of tubes can remain independent as they extend through the connector. In use, a chilled fluid can be circulated through a plurality of fluid loops defined by the tubes to apply a regional cooling effect to tissue against which the tubes are positioned. As shown in FIG. 44, the tubes 158 can be positioned in loop shapes having a reduced lateral diameter and an enlarged longitudinal diameter to facilitate insertion or removal of the device 102 through a cylindrical tissue opening having a small radius. As shown in FIG. 45, the tubes 158 can be transitioned (e.g., by pushing the connector 160 distally) to loop shapes having an enlarged lateral diameter and a reduced longitudinal diameter to spread the cooling mesh defined by the tubes radially outward over a treatment site. The plurality of loops can thus collectively define an ellipsoid wireframe (e.g., a prolate spheroid as shown in FIG. 44 or an oblate spheroid as shown in FIG. 45). When it is desired to remove the implanted device 102, a proximally-directed pulling force can be applied to the connector 160 to withdraw the connector and bend the tubes 158 into the configuration shown in FIG. 44 such that they can be extracted through the tissue opening formerly occupied by the connector. This can advantageously allow for easy post-operative removal of the device in a non-invasive or minimally-invasive manner.

As noted above, the thermal device can include an inner reservoir or chamber. The chamber can house at least a portion of the elements, volumes, nozzles, fluid lumens, channels, paths, and so forth needed to support the cooling means.

In implementations in which the cooling means includes expanding gas, the thermal device can include an expansion nozzle through which gas that has entered the thermal device via a cooling delivery conduit expands. The gas is expanded into the chamber, from which it can be exhausted from the thermal device via an exhaust conduit. The expanded gas can be exhausted into the environment, into a chamber or tank, or into a compressor which re-compresses it.

In implementations in which the cooling means is a chilled fluid, the fluid can be passed through the inner chamber of the thermal device to deliver a cooling effect thereto and to surrounding tissue. In some embodiments, the chamber can be in the form of a fluid lumen having a first end coupled to a delivery conduit and a second end coupled to an exhaust conduit. The chamber/fluid lumen can optionally be coiled, snaked, or formed in some other tortuous, surface-area maximizing shape such that heat exchange to/from fluid that is directed through the chamber can be optimized. The fluid can also simply enter the chamber through a delivery conduit, reverse direction, and exit the thermal device through an exhaust conduit.

In implementations in which the cooling means is a Peltier device, the Peltier device can be embedded inside the thermal device and electrical lines can be connected to the Peltier device internal to the thermal device. These electrical lines can extend from the thermal device to a power source and optionally a regulator of the cooling effect, which can regulate the voltage or current on the electrical lines. In some embodiments, the power source and/or regulator can be disposed on or in the thermal device or in a separate implantable unit.

The thermal device can optionally include a plurality of thermal fins formed within the chamber. For example, the thermal fins can extend radially inward from an outer wall of the chamber. In use, an expanded gas or chilled fluid can circulate around and across the thermal fins, which can improve the thermal conduction from the cooling means to the thermal device, and thus to the target tissue. The thermal fins can also improve the mechanical strength of the thermal device. It will be appreciated that the thermal fins can be oriented in a variety of directions and can take on a variety of shapes and sizes.

The delivery conduit can extend well into the chamber, terminating at a location adjacent to a distal end of the chamber. The exhaust conduit, on the other hand, can terminate only a small distance into the chamber, adjacent to the proximal end thereof. With this relative positioning of the conduit outlets, fluid introduced through the delivery conduit must flow through substantially the entire length of the chamber before being removed through the exhaust conduit. In this manner, the thermal transfer between the fluid and the thermal device can be maximized and more evenly distributed along the heat exchanging surfaces of the thermal device. In some embodiments, the chamber and/or the delivery conduit can extend only along discrete portions of the device where cooling is desired.

In some embodiments, the delivery conduit can be helically wound around the perimeter of the chamber. This can advantageously improve thermal transfer between the delivery conduit and the thermal device. In addition, the delivery conduit can act as an internal baffle, routing fluid released from the distal end of the delivery conduit along a helical path back towards the exhaust conduit. Thus, thermal transfer can also be improved between fluid released from the delivery conduit and the thermal device.

Portions of the thermal device other than the regions to be placed against the target anatomy can be coated with a thermally insulating material, such that the cooling effect is focused at the target site, such that surrounding tissue is protected from the cooling effect, and such that a surgeon or other user holding the device is protected from the cooling effect. Exemplary thermally insulating materials include silicone, which can be spray coated onto the device.

It will be appreciated that the devices and hardware described herein are able to be produced using common practices known to those skilled in the art of hardware manufacturing and specifically surgical device manufacturing.

Methods

The thermal devices disclosed herein can be used in any of a variety of associated methods. Various examples of such methods are described below. It should be noted that any ordering of method steps implied by the following is not to be construed as limiting the method to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present invention. Furthermore, two or more of the method steps can be performed simultaneously.

Before beginning a surgical procedure, a surgical plan can be developed, for example using pre-operative imaging of the site that is targeted for thermal therapy (e.g., cooling and/or heating). A thermal device having an appropriate type, size, shape, etc. can be selected as part of the surgical plan, or can be selected in real-time during the actual surgery. As detailed above, the particular thermal device to be used can be selected based on a variety of factors.

Access to the target site can be obtained using various known techniques. For example, a tissue opening can be formed using an open surgical technique (e.g., one in which skin, fat, muscle, connective tissue, etc. overlying the surgical site is incised and retracted). A tissue opening can also be formed using a minimally-invasive surgical technique (e.g., one in which a percutaneous access device is used to form a portal between the patient's skin surface and the target site).

Various steps can be performed to prepare the target site for thermal therapy. For example, in the case of a traumatic spinal cord injury, a decompression procedure (e.g., partial or complete laminectomy) can be performed at one or more vertebral levels. By way of further example, the site can be prepared by decorticating bone in the vicinity of the target site. Thus, in the case of a spinal procedure, the surfaces of the lamina, spinous process, and/or facets can be decorticated.

Various ancillary or related procedures can be performed at the target site before or after initiating thermal therapy. For example, a spinal fusion procedure or a procedure to install spinal stabilization hardware can be performed.

The steps involved in placing the thermal device and applying thermal therapy therewith vary depending on the type of thermal device that is used.

In some embodiments, a connectionless thermal device (e.g., of the type shown in FIG. 2) is pre-chilled or pre-heated and then placed on the target site (e.g., the exposed dura or spinal cord of the patient). Placement of the thermal device can include conforming the device to the target anatomy. Correct placement of the device can be verified visually or using fluoroscopy or other imaging techniques. Embedded sensors can be used to monitor various parameters of the patient or operating environment, and the thermal therapy can be modulated based on the output of the sensors. For example, if sensed temperature at the target site drops below a desired level, the thermal device can be lifted off of the target site or removed from the target site. On the other hand, if the sensed temperature at the target site rises above a desired level, the thermal device can be removed and re-chilled, or can be replaced with another pre-chilled thermal device. Once the desired duration of thermal therapy is attained, the device can be removed from the target site and the tissue opening can be closed. An implantable, active thermal device can optionally be implanted prior to closing the tissue opening for chronic delivery of thermal therapy.

In some embodiments, a passive connectionless thermal device (with or without pre-chilling or pre-heating) is placed on the target site (e.g., the exposed dura or spinal cord of the patient). Placement of the thermal device can include conforming the device to the target anatomy. Correct placement of the device can be verified visually or using fluoroscopy or other imaging techniques. The passive thermal device can be cooled by an active cooling system, which can be disposed external to the patient. Exemplary active cooling systems include heat exchangers, fluid coils, Peltier devices, ice packs, etc. Embedded sensors can be used to monitor various parameters of the patient or operating environment, and the thermal therapy can be modulated based on the output of the sensors. For example, if sensed temperature at the target site drops below a desired level, the active cooling applied through the thermal device can be reduced. On the other hand, if the sensed temperature at the target site rises above a desired level, the active cooling applied through the thermal device can increased. Once the desired duration of thermal therapy is attained, the device can be removed from the target site and the tissue opening can be closed. An implantable, active thermal device can optionally be implanted prior to closing the tissue opening for chronic delivery of thermal therapy.

In some embodiments, a thermal device having one or more penetrable regions (e.g., of the type shown in FIGS. 14-17) is placed on the target site (e.g., the exposed dura or spinal cord of the patient). The device can be placed initially while in a collapsed, rolled-up, and/or deflated configuration (e.g., through a minimally-invasive pathway). A connector can be inserted through a penetrable region of the device to allow application, removal, or circulation of cooling media before or after the device is placed at the target site. A single connector housing inlet and exhaust conduits can be used, or multiple connectors (e.g., one for inlet and one for exhaust) can be inserted through the same or different penetrable areas. In some embodiments, a single connector having a single conduit can be used, in which case media application and removal steps can be performed serially through the same lumen. If the device is initially placed in a collapsed configuration, fluid can be delivered through a fluid inlet conduit of the connector to inflate the device to the desired size or shape.

Placement of the thermal device can include conforming the device to the target anatomy. Placement of the thermal device can also include pulling or otherwise manipulating one or more tethers extending from the device to adjust a position or orientation of the device. Correct placement of the device can be verified visually or using fluoroscopy or other imaging techniques. Placement of the thermal device can also include anchoring or clamping the device to the patient anatomy or to a device, implant, etc. at the target site (e.g., using attachment features like those shown in FIGS. 37-41).

Thermal therapy can be applied through the device, for example by circulating a chilled fluid through the device. The device can include a reservoir filled with gel or some other substrate material, in which case the fluid can be circulated through the gel or substrate. Embedded sensors can be used to monitor various parameters of the patient or operating environment, and the thermal therapy can be modulated based on the output of the sensors. For example, the temperature and/or flow rate of fluid circulated through the device can be adjusted to maintain a desired temperature. Where only intraoperative therapy is desired, the device can be removed once the desired duration of thermal therapy has been applied and the tissue opening can be closed. Where postoperative therapy is desired, the thermal device and one or more connectors can be left in place and the tissue opening can be closed. The one or more connectors can be left exposed, extending through the closed tissue opening. The one or more connectors can also be left buried beneath the patient's skin, where they are readily accessible in a minimally-invasive follow on procedure to conduct additional thermal therapy or to remove the one or more connectors. In either case, the connectors can be sutured or otherwise secured to prevent excessive movement or inadvertent expulsion. Postoperative thermal therapy can be delivered through the one or more connectors for an extended period, as described in more detail below. When the capability to deliver additional thermal therapy is no longer desired, the one or more connectors can be removed (e.g., by pulling them proximally to withdraw them from the penetrable regions of the device). The thermal device can be left implanted permanently, and can optionally be configured to be bioabsorbed by the patient over time. Alternatively, the thermal device can be removed, for example by evacuating fluid from the device (e.g., using compressed air or vacuum suction) and then collapsing the device for removal through the small opening left when the connectors are removed (e.g., without reopening the tissue opening). A tether can be used to pull out the collapsed device. Any remaining tissue opening can then be closed.

In some embodiments, a thermal device having pre-attached tubing or conduits (e.g., of the type shown in FIG. 25) is placed on the target site (e.g., the exposed dura or spinal cord of the patient). The device can be placed initially while in a collapsed, rolled-up, and/or deflated configuration (e.g., through a minimally-invasive pathway). If the device is initially placed in a collapsed configuration, fluid can be delivered through a fluid inlet conduit to inflate the device to the desired size or shape.

Placement of the thermal device can include conforming the device to the target anatomy. Placement of the thermal device can also include pulling or otherwise manipulating the pre-attached tubing or one or more tethers extending from the device to adjust a position or orientation of the device. Correct placement of the device can be verified visually or using fluoroscopy or other imaging techniques. Placement of the thermal device can also include anchoring or clamping the device to the patient anatomy or to a device, implant, etc. at the target site (e.g., using attachment features like those shown in FIGS. 37-41).

Thermal therapy can be applied through the device, for example by circulating a chilled fluid through the device. The device can include a reservoir filled with gel or some other substrate material, in which case the fluid can be circulated through the gel or substrate. Embedded sensors can be used to monitor various parameters of the patient or operating environment, and the thermal therapy can be modulated based on the output of the sensors. For example, the temperature and/or flow rate of fluid circulated through the device can be adjusted to maintain a desired temperature. Where only intraoperative therapy is desired, the device can be removed once the desired duration of thermal therapy has been applied and the tissue opening can be closed. Where postoperative therapy is desired, the thermal device and the tubing attached thereto can be left in place and the tissue opening can be closed. The tubing can be left exposed, extending through the closed tissue opening. The tubing can also be left buried beneath the patient's skin, where it is readily accessible in a minimally-invasive follow on procedure to conduct additional thermal therapy or to remove the tubing or device. In either case, the tubing can be sutured or otherwise secured to prevent excessive movement or inadvertent separation. Postoperative thermal therapy can be delivered through the tubing for an extended period, as described in more detail below. When the capability to deliver additional thermal therapy is no longer desired, the tubing can be removed. Any of the techniques described above can be used to separate the tubing from the device, including breaking a frangible portion of the tubing by exerting a proximally directed pulling force, pulling a tether to tear the tubing, or allowing at least a portion of the tubing to be bioabsorbed by the patient. The thermal device can be left implanted permanently, and can optionally be configured to be bioabsorbed by the patient over time. Alternatively, the thermal device can be removed, for example by evacuating fluid from the device (e.g., using compressed air or vacuum suction) and then collapsing the device for removal through a small tissue opening (e.g., without reopening the tissue opening). The tubing or a tether can be used to pull out the collapsed device. Any remaining tissue opening can then be closed.

Figure 46:
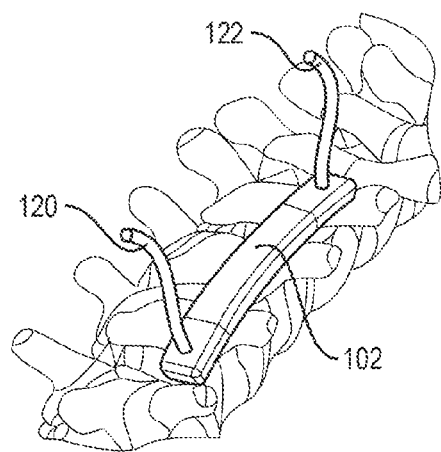
FIG. 46 is a perspective view of a rectangular thermal device positioned across multiple levels of a patient's spinal column.
Figure 47:
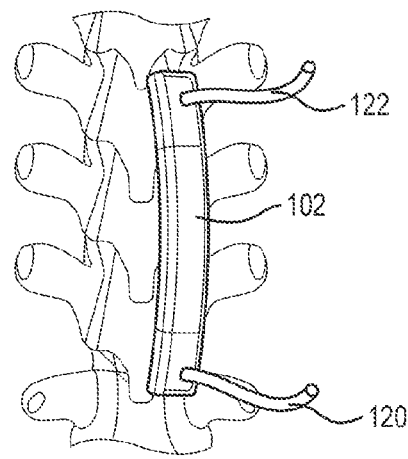
FIG. 47 is a profile view of the thermal device and spinal column of FIG. 41.

In an exemplary method, as shown in FIGS. 46-47, a rectangular thermal device 102 having pre-attached inlet and outlet conduits 120, 122 can be positioned over multiple levels of a patient's spinal column.

In some embodiments, a thermal device having a connector that can be selectively coupled or decoupled to/from a port of the thermal device (e.g., of the type shown in FIGS. 26-28) is placed on the target site (e.g., the exposed dura or spinal cord of the patient). The device can be placed initially while in a collapsed, rolled-up, and/or deflated configuration (e.g., through a minimally-invasive pathway). A connector can be attached to a port of the device to allow application, removal, or circulation of cooling media, before or after the device is placed at the target site. A single connector housing inlet and exhaust conduits can be used, or multiple connectors (e.g., one for inlet and one for exhaust) can be coupled to ports on the device. In some embodiments, a single connector having a single conduit can be used, in which case media application and removal steps can be performed serially through the same lumen. If the device is initially placed in a collapsed configuration, fluid can be delivered through a fluid inlet conduit of the connector to inflate the device to the desired size or shape.

Placement of the thermal device can include conforming the device to the target anatomy. Placement of the thermal device can also include pulling or otherwise manipulating a connector coupled thereto or one or more tethers extending from the device to adjust a position or orientation of the device. Correct placement of the device can be verified visually or using fluoroscopy or other imaging techniques. Placement of the thermal device can also include anchoring or clamping the device to the patient anatomy or to a device, implant, etc. at the target site (e.g., using attachment features like those shown in FIGS. 37-41).

Thermal therapy can be applied through the device, for example by circulating a chilled fluid through the device. The device can include a reservoir filled with gel or some other substrate material, in which case the fluid can be circulated through the gel or substrate. Embedded sensors can be used to monitor various parameters of the patient or operating environment, and the thermal therapy can be modulated based on the output of the sensors. For example, the temperature and/or flow rate of fluid circulated through the device can be adjusted to maintain a desired temperature. Where only intraoperative therapy is desired, the device can be removed once the desired duration of thermal therapy has been applied and the tissue opening can be closed. Where postoperative therapy is desired, the thermal device and the one or more connectors coupled thereto can be left in place and the tissue opening can be closed. The one or more connectors can be left exposed, extending through the closed tissue opening. The one or more connectors can also be left buried beneath the patient's skin, where they are readily accessible in a minimally-invasive follow on procedure to conduct additional thermal therapy or to remove the one or more connectors and/or the device. In either case, the one or more connectors can be sutured or otherwise secured to prevent excessive movement or inadvertent decoupling. Postoperative thermal therapy can be delivered through the one or more connectors for an extended period, as described in more detail below. When the capability to deliver additional thermal therapy is no longer desired, the one or more connectors can be removed. Any of the techniques described above can be used to decouple the connectors from the device, including decoupling a snap-fit, compression fit, or threaded connection between the connector and the device port. The thermal device can be left implanted permanently, and can optionally be configured to be bioabsorbed by the patient over time. Alternatively, the thermal device can be removed, for example by evacuating fluid from the device (e.g., using compressed air or vacuum suction) and then collapsing the device for removal through a small tissue opening (e.g., without reopening the tissue opening). The one or more connectors or a tether can be used to pull out the collapsed device. Any remaining tissue opening can then be closed.

Figure 48:
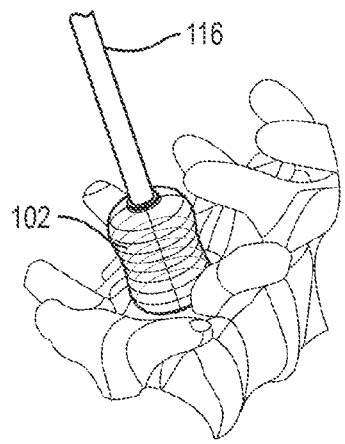
FIG. 48 is a perspective view of a cylindrical thermal device positioned over a patient's dura.

In an exemplary method, as shown in FIG. 48, a cylindrical thermal device having a port on its proximal-facing end surface can be positioned over a patient's dura after a laminectomy. The connector 116 can be positioned to extend from the proximal end of the thermal device to a point external to the patient, where it can be coupled to the thermal source 104.

In some embodiments, a thermal device having a plurality of bendable or deformable loops of tubing (e.g., of the type shown in FIGS. 42-45) is placed on the target site (e.g., the exposed dura or spinal cord of the patient). The device can be inserted initially through a tissue opening the with tube loops bent into a longitudinally-extended position (e.g., as shown in FIG. 44 for insertion through a minimally-invasive pathway).

Placement of the thermal device can include conforming the loops of tubing to the target anatomy, for example by bending the loops of tubing to the position shown in FIG. 45 such that a mesh of tubing is formed over the target site. Placement of the thermal device can also include pulling or otherwise manipulating a connector coupled to the loops of tubing or one or more tethers extending from the device to adjust a position or orientation of the device. Correct placement of the device can be verified visually or using fluoroscopy or other imaging techniques. Placement of the thermal device can also include anchoring or clamping the device to the patient anatomy or to a device, implant, etc. at the target site.

Thermal therapy can be applied through the device, for example by circulating a chilled fluid through the loops of tubing. Embedded sensors can be used to monitor various parameters of the patient or operating environment, and the thermal therapy can be modulated based on the output of the sensors. For example, the temperature and/or flow rate of fluid circulated through the device can be adjusted to maintain a desired temperature. Where only intraoperative therapy is desired, the device can be removed once the desired duration of thermal therapy has been applied and the tissue opening can be closed. Where postoperative therapy is desired, the thermal device and the one or more connectors coupled thereto can be left in place and the tissue opening can be closed. The one or more connectors can be left exposed, extending through the closed tissue opening. The one or more connectors can also be left buried beneath the patient's skin, where they are readily accessible in a minimally-invasive follow on procedure to conduct additional thermal therapy or to remove the one or more connectors and/or the device. In either case, the one or more connectors can be sutured or otherwise secured to prevent excessive movement. Postoperative thermal therapy can be delivered through the one or more connectors for an extended period, as described in more detail below. When the capability to deliver additional thermal therapy is no longer desired, the loops of tubing can be removed, for example by pulling the connector proximally out of the patient to bend the loops of tubing into the shape shown in FIG. 44 such that they can be withdrawn through the opening formerly occupied by the connector. Any remaining tissue opening can then be closed. Alternatively, the thermal device can be left implanted permanently, and can optionally be configured to be bioabsorbed by the patient over time.

Figure 49:
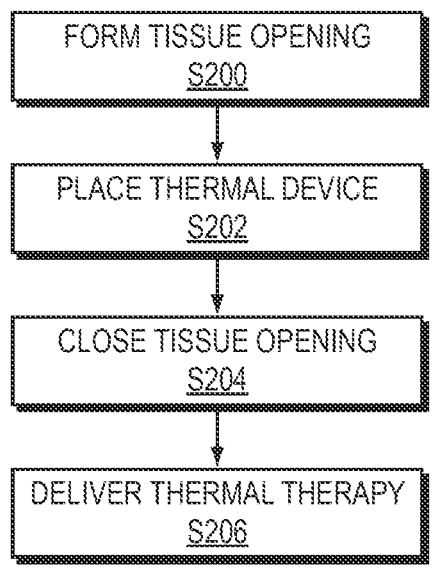
FIG. 49 is a flow chart of an exemplary method of applying thermal therapy.
Figure 50:
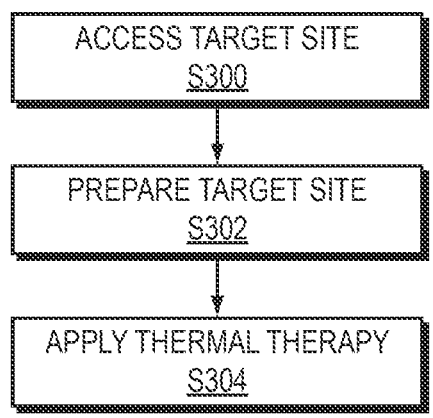
FIG. 50 is a flow chart of another exemplary method of applying thermal therapy.

FIG. 49 illustrates a method of applying thermal therapy to tissue. In step S200, a tissue opening is formed. A thermal device is placed at a target site in step S202 and the tissue opening is closed in step S204. After closing the tissue opening, thermal therapy is delivered to the target site via the thermal device in step S206. Thermal therapy can also be initiated or delivered via the thermal device prior to closing the tissue opening in step S204, and can be continued or re-started in step S206 after closing the tissue opening. FIG. 50 illustrates a method of applying thermal therapy to tissue. In step S300, a target site is accessed. The target site is prepared in step S302, and thermal therapy is applied to the target site via a thermal device in step S304.

The thermal device can be left implanted for any amount of time (e.g., at least about 1 hour, at least about 4 hours, at least about 12 hours, at least about 18 hours, at least about 24 hours, at least about 48 hours, at least about 72 hours, at least about 5 days, at least about 7 days, at least about 2 weeks, at least about 1 month, at least about 3 months, at least about 6 months, at least about 1 year, at least about 5 years, at least about 10 years, and/or permanently or indefinitely.

Hypothermia Delivery—Temperature & Time

The methods and devices described herein can generally involve applying localized therapeutic hypothermia and, in some cases, cooling the tissue in and around the spinal cord. Various hypothermic instrumentations are described to deliver a cooling effect to the spinal canal, and to the spinal cord itself. "Therapeutic hypothermia" as used herein refers to the reduction of tissue temperature below a patient's normal body temperature, typically about 37 degrees C. Therapeutic hypothermia can also include reduction of tissue temperature below a patient's body temperature when treatment is initiated, which may not be the patient's normal body temperature (e.g., when the patient presents with a fever or in an already-hypothermic state, for example due to previous or ongoing systemic hypothermia treatment).

The degree of hypothermia applied can vary upon a number of factors. Target therapeutic temperatures can range from just below 0 degrees C. to just below normothermia. Tissue exposure to temperatures below 0 degrees C. can lead to cellular damage, however the bones of the spinal column are relatively resilient to such low temperatures and therefore target therapeutic temperatures can be below 0 degrees C. in some embodiments.

In an exemplary embodiment, the target tissue is cooled to within a range of about 0 degrees C. to about 37 degrees C. The target tissue can also be cooled to within a range of about 5 degrees C. to about 36 degrees C., more preferably about 15 degrees C. to about 36 degrees C., more preferably about 25 degrees C. to about 36 degrees C., more preferably about 25 degrees C. to about 35 degrees C., and more preferably about 30 degrees C. to about 34 degrees C. In certain embodiments, the target tissue can be cooled to about 36 degrees C., about 35 degrees C., about 34 degrees C., about 33 degrees C., about 32 degrees C., about 31 degrees C., or about 30 degrees C. In other aspects, the target tissue can be cooled to about 1 degree C. below normothermia, about 2 degrees C. below normothermia, about 5 degrees C. below normothermia, about 10 degrees C. below normothermia, or about 20 degrees C. below normothermia.

Degrees of hypothermia are sometimes described in terms of "mild" hypothermia (e.g., 0-5 degrees C. below normothermia), "moderate" hypothermia (e.g., 5-9 degrees C. below normothermia), "severe" hypothermia (e.g., 9-17 degrees C. below normothermia), and "profound" hypothermia (e.g., more than 17 degrees C. below normothermia). The methods disclosed herein can include cooling of tissue to within any of these ranges, and the systems and devices disclosed herein can be configured to achieve such cooling. Various treatment protocols can also be used in which the tissue temperature is cycled, pulsed, swept, ramped, and/or stepped through these or other ranges. For example, in one treatment method, the tissue temperature can be quickly lowered to a target temperature and then slowly ramped back up to normothermia when it is desired to cease treatment. By way of further example, the tissue temperature can be slowly stepped down to a first target temperature, oscillated between the first target temperature and a second target temperature, and then eventually stepped back up to normothermia.

The duration of exposure of the target tissue to the cooling effect can range from minutes to days, weeks, months, or years depending on a variety of factors, including the patient's condition, the treatment of the patient's other injuries, the prospective treatment protocol for the patient, and monitored or detectable physiological responses, or lack thereof, to the cooling. Therapeutic hypothermia can be applied in a single procedure or multiple times. In either case, a multiplicity of different temperatures can be applied. Preferably, when discussing target temperatures, it is intended to mean the desired therapeutic temperature of the targeted tissue. Alternatively, target temperature at times can also refer to the temperature of the thermal device or the cooling chamber or element of the thermal device. It will be appreciated that it can be necessary in some instances to cool the thermal device to below the target tissue temperature in order for the target tissue to reach the target tissue temperature.

The methods described herein can include cooling the spinal canal tissue and the spinal cord for variable lengths of time and/or at different temperatures. In addition, cooling can occur in multiple doses, where each dose can differ from the others in exposure time and/or temperature. The determination of the exposure time(s) and temperature(s) can be predetermined based on known effective times and temperatures or can be determined based on the condition of the patient and/or when the treatment is applied relative to when the injury occurred. A wide variety of physiological effects, both local and systemic, can arise from the cooling of the target tissue (e.g., spinal canal tissue and the spinal cord) below normal body temperature. Exposure time, doses, and target temperature can be varied during the procedure based on monitored physiological parameters or characteristics as well as parameters of the cooling devices or systems.

These parameters include, but are not limited to, neurological findings, blood pressure, target-tissue temperature, specific tissue temperature (proximate to target tissue), core (rectal) body temperature, venous blood temperature near or exiting target tissue, pulmonary conditions, cardiac conditions, sensory evoked potentials (SEPs, including somatosensory evoked potentials), motor-evoked potentials (MEPs), intrathecal pressure, perfusion pressure, levels of blood oxygen & glucose, ATP concentrations, markers of excitotoxicity, vasogenic edema, apoptosis, inflammation, and enzymatic responses. The target temperature, doses, and exposure time can be selected by initial measurements of these physiological parameters and then modified based upon real-time measurement of these parameters. Effectively, the cooling regimen, in terms of temperatures, exposure times, and doses, can be controlled by measured physiological characteristics of the patient and the cooling devices and systems.

For example, a cooling effect can be applied initially at a predetermined target temperature based on the type and severity of injury incurred, including for example the vertebral level of injury. The cooling effect can be increased, and as such, the target temperature can be reduced, if after a predetermined period of time, the motor-evoked potential responses of the patient appear unremarkable. In one embodiment, if the difference between the arterial blood pressure and the cerebral spinal fluid pressure reduces below a predetermined threshold, the application of the therapeutic hypothermia can be stopped. It should be understood that there are any number of protocols that can be followed in the application of therapeutic hypothermia based on clinical, laboratory, and monitoring markers.

In one embodiment, therapeutic hypothermia is initiated as soon as possible following a spinal injury, e.g., less than 8 hours after the injury. Therapeutic hypothermia can be maintained up to 72 hours, up to 120 hours, or more. It can be desirable to deliver therapeutic hypothermia for a much shorter duration as well, including as little as a fraction of an hour (e.g., 5 minutes, 15 minutes, 30 minutes, or 45 minutes).

The use of therapeutic hypothermia on the spinal cord and the spinal canal can yield a variety of beneficial effects. Such effects can include the reduction of nervous tissue metabolic demand, excitotoxic markers, apoptosis, free-radicals, and inflammation. It should be noted that some of the mechanisms of action associated with therapeutic hypothermia are not fully understood, but experience with its application in a variety of clinical situations suggests a mitigating effect in spinal cord damage from trauma, vascular insult, or surgical insult.

Transosseous Cooling

In some of the methods and devices described herein, a cooling effect is applied transosseously, or through bone. In particular, tissue can be cooled by positioning a thermal device over adjacent or nearby bone or over an implant implanted in adjacent or nearby bone. Bone has properties that make it an advantageous cooling platform. Boney structures are readily locatable due to their greater density and rigidity than so-called soft tissues. Furthermore, their geometries are readily mapped radiographically, are relatively consistent between patients, and have easily locatable features or landmarks. Accordingly, particular surrounding or soft tissues are relatively consistently located in a known proximity to these bone structures and landmarks. In particular, vertebral pedicles and lamina lie in close proximity to the contents of the spinal canal, including the spinal cord and nerve roots.

These attributes allow specific surrounding soft tissue to be reliably targeted by using adjacently located bone structures and landmarks of the bone structures as a platform and avenue to put devices near the specific soft tissue. Using bony structures and their landmarks as a means for targeting nearby or adjacent tissues helps avoid a need to directly target the tissue wishing to be treated, leaving the tissue undisturbed.

An advantageous aspect of a transosseous approach for providing a cooling effect to nearby soft tissue is the fact that bone is rigid, allowing for an device to be securely anchored into or on the bone, where the bone is not subject to deformation because of bodily movement or because of the device's presence. The rigid nature of the bone also allows a thermal device applied or anchored thereto without disturbing the tissues outside of the bone.

A transosseous approach for providing a cooling effect to nearby soft tissue allows for the implantation of thermal instrumentation without disturbing the soft tissue itself. That is, by using a bone approach and cooling across the bone wall to the nearby tissue, the targeted nearby tissue is not physically touched, displaced, or incised by the thermal device or by the surgical steps needed to implant the thermal device. Certain tissues, such as spinal cord tissue, are delicate and sensitive to disturbances, and such disturbances could cause permanent injury to the tissues. As such, it can be undesirable to implant thermal devices in these tissues or in nearby soft tissues due to risks of causing injury to the tissues. Bone is very resilient to such disturbances, and typically does not realize a great loss in function or strength and is typically not susceptible to long term injury from such disturbances. It is therefore desirable to apply or affix a thermal device to a bony structure and cool nearby soft tissue transosseously, or across the bone wall, thus allowing for reliable cooling access to soft tissue without physically disturbing the soft tissue itself.

In exemplary embodiments, the soft tissue that is targeted to be cooled is the spinal cord, other spinal canal tissue, and/or nerve root tissue, and the bony structures which act as the cooling platform are parts of a vertebra, including the elements of the posterior arch such as the pedicles, the lamina, and the spinous process. A transosseous approach for providing cooling across pedicle and/or lamina bone to the adjacent spinal canal contents targets the spinal cord without its actual contact, displacement, or penetration. This can be a critical consideration since the spinal cord's tolerance for such intrusions is likely minimal. In some embodiments, however, particularly those in which a decompression procedure is performed, the thermal devices can be placed in direct contact with the spinal cord or the dura.

Concluding Statements

It will be understood that any of the methods and devices disclosed herein can be used on multiple vertebrae at once and/or multiple bony structures of each vertebra at once, by utilizing multiple thermal devices at the same time or a single, larger thermal device. It will be understood that the methods and devices disclosed herein can be used for conditions other than traumatic spinal cord injury, including for cooling other tissues. The methods and devices can be used for other types of spinal cord injury, as well as for treating nerve root damage. The methods and devices can be used prophylactically. The methods and devices can be used before, during, and/or after an injury occurs and can be used pre-operatively, peri-operatively, intra-operatively and/or post-operatively with regard to any particular procedure that can be conducted.

Furthermore, the methods and devices can be used for non-injury related purposes. In particular, the methods and devices described herein can be used as an adjunctive procedure to an aneurysm repair surgery, such as thoracoabdominal aortic aneurysm repair or abdominal aortic aneurysm repair. In these procedures, it is common for blood flow to the spinal cord to be compromised, thus introducing a risk of ischemic spinal cord injury. The methods and devices described herein can provide a protective therapy during such ischemic periods.

Further, the methods and devices described herein can also be used for spinal fusion procedures where cooling is not initially intended. The methods and devices described herein can be used for fusion with the understanding that an intraoperative complication can occur (example: iatrogenic injury caused during scoliosis correction surgery) where having the capability to deliver a cooling effect can be desired.

The methods and devices described herein can be used prophylactically to deliver a cooling effect to nerve roots. Though such delivery of a cooling effect can be achieved with one thermal device, it can be better achieved by having two or more thermal devices placed above and below the particular root that is being targeted. The delivery of a cooling effect to a nerve root can also occur peri-operatively or post-operatively.

It will be appreciated that the methods and devices disclosed herein can be used in other parts of a mammalian body, and in particular, can be used with orthopedic procedures to deliver a cooling effect to surrounding tissues.

The described aspects above are given as illustrative examples of those that fall within the scope of the subject matter described, but are not intended to limit that scope. The described devices and methods can be the sole devices and methods used and performed in the spine at the time of the herein described therapy or can accompany other devices and procedures such as those related to spinal decompression, reduction, stabilization, and fusion.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used device is obtained and if necessary cleaned. The device can then be sterilized. In one sterilization technique, the device is placed in a closed and sealed container, such as a plastic or TYVEK bag. The container and its contents are then placed in a field of radiation that can penetrate the container, such as gamma radiation, x-rays, or high-energy electrons. The radiation kills bacteria on the device and in the container. The sterilized device can then be stored in the sterile container. The sealed container keeps the device sterile until it is opened in the medical facility.

Further details on methods and devices for cooling tissue, including methods and devices which can be used in conjunction with those described herein, are discussed in U.S. Pat. No. 8,523,930 issued on Sep. 3, 2013, entitled "METHODS AND DEVICES FOR COOLING SPINAL TISSUE," and U.S. application Ser. No. 13/751,503 (which is expected to issue as U.S. Pat. No. 8,721,642 on May 13, 2014), entitled "TISSUE COOLING CLAMPS AND RELATED METHODS," which are hereby incorporated by reference herein in their entirety.

The foregoing description has been presented for purposes of illustration and description. Many modifications and variations of the subject matter described will be apparent to those skilled in the art. Although the invention has been described by reference to specific embodiments, it should be understood that numerous changes can be made within the spirit and scope of the inventive concepts described. Accordingly, it is intended that the invention not be limited to the described embodiments, but that it have the full scope defined by the language of the following claims.

What is claimed is:

1. A method of applying thermal therapy to tissue, comprising:
   forming a tissue opening in a patient to access a target site within the patient;
   passing a thermal device through the tissue opening;
   placing the thermal device at the target site;
   closing the tissue opening with the thermal device at the target site;
   after closing the tissue opening, applying or continuing to apply thermal therapy to the target site through the thermal device; and
   after closing the tissue opening, pulling a tether attached to the thermal device to remove the thermal device from the patient without reopening the tissue opening;
   wherein the thermal device comprises a malleable pad.

2. The method of claim 1, wherein forming the tissue opening comprises forming a minimally invasive pathway that extends from external to the patient to the target site.

3. The method of claim 1, further comprising preparing the target site by at least one of decorticating bone, performing a laminectomy procedure, and installing spinal fixation implants.

4. The method of claim 1, wherein placing the thermal device comprises at least one of positioning the thermal device over the posterior side of a vertebra such that the device extends between the transverse processes of the vertebra, positioning the thermal device at one or more vertebrae, positioning the thermal device in contact with the posterior side of a vertebra, positioning the thermal device in contact with a lamina, positioning the thermal device in contact with a spinous process, and positioning the thermal device in contact with a transverse process.

5. The method of claim 1, wherein the placing the thermal device comprises positioning the device between the spinous processes and transverse processes of multiple vertebrae.

6. The method of claim 1, wherein placing the thermal device comprises conforming a malleable outer membrane of the thermal device to the target site.

7. The method of claim 1, wherein placing the thermal device comprises placing the thermal device while it is partially or completely empty and wherein the method further comprises filling the thermal device with media to inflate the thermal device to a desired size or shape.

8. The method of claim 1, wherein placing the thermal device comprises placing the thermal device while it is partially or completely empty and wherein the method further comprises filling the thermal device with media to inflate the thermal device to a desired size or shape after closing the tissue opening.

9. The method of claim 1, further comprising expanding the thermal device into contact with the target site by supplying fluid thereto.

10. The method of claim 1, wherein the target site comprises an at least partially exposed dura of the patient's spinal cord.

11. The method of claim 1, wherein placing the thermal device comprises positioning the thermal device in direct contact with a spinal implant implanted in the patient to apply thermal therapy to a spinal cord and surrounding tissue of the patient through the spinal implant.

12. The method of claim 1, further comprising, after closing the tissue opening, pulling the tether attached to the thermal device, the tether extending through the closed tissue opening, to adjust a position of the thermal device relative to the target site.

13. The method of claim 1, wherein passing the thermal device through the tissue opening comprises passing the thermal device while it is in a collapsed, flattened, or rolled configuration.

14. The method of claim 1, further comprising inserting a connector that defines a fluid inlet lumen and a fluid outlet lumen through a penetrable area of the thermal device, wherein applying the thermal therapy comprises circulating a fluid through the fluid inlet lumen, the thermal device, and the fluid outlet lumen.

15. The method of claim 1, further comprising coupling a connector having a mating feature to a port of the thermal device that includes a counterpart mating feature.

16. The method of claim 1, further comprising coupling the thermal device to at least one of patient anatomy and an implant.

17. The method of claim 1, further comprising inserting a bone fastener through the thermal device to couple the thermal device to a vertebra.

18. The method of claim 1, wherein closing the incision comprises closing the incision such that at least one fluid lumen coupled to the thermal device extends through the closed incision.

19. The method of claim 1, wherein applying the thermal therapy comprises at least one of circulating a chilled fluid through the thermal device, circulating a heated fluid through the thermal device, expanding a gas within the thermal device, and applying electrical current to a Peltier device disposed in the thermal device.

20. The method of claim 1, further comprising circulating fluid through an inner reservoir of the thermal device, the inner reservoir being at least partially filled with a gel or substrate.

21. The method of claim 1, wherein applying the thermal therapy comprises applying the thermal therapy over a period of at least about 1 hour.

22. The method of claim 1, wherein applying the thermal therapy comprises applying the thermal therapy over a period of at least about 4 hours.

23. The method of claim 1, wherein applying the thermal therapy comprises applying the thermal therapy over a period of at least about 8 hours.

24. The method of claim 1, wherein applying the thermal therapy comprises applying the thermal therapy over a period of at least about 24 hours.

25. The method of claim 1, wherein applying the thermal therapy comprises applying the thermal therapy over a period of at least about 3 days.

26. The method of claim 1, further comprising, after closing the tissue opening, transitioning the thermal device to at least one of a rolled configuration, a radially-collapsed configuration, and a longitudinally collapsed configuration and removing the thermal device from the patient.

27. A method of applying thermal therapy to tissue, comprising:
   forming a tissue opening in a patient to access a target site within the patient;
   passing a thermal device through the tissue opening;
   placing the thermal device at the target site;
   closing the tissue opening with the thermal device at the target site;
   after closing the tissue opening, applying or continuing to apply thermal therapy to the target site through the thermal device; and
   after closing the tissue opening, emptying fluid from the thermal device, collapsing or rolling the thermal device, and removing the thermal device through the closed tissue opening without reopening the tissue opening;
   wherein the thermal device comprises a malleable pad.

28. A method of applying thermal therapy to tissue, comprising:
   forming a tissue opening in a patient to access a target site within the patient;
   passing a thermal device through the tissue opening;
   placing the thermal device at the target site;
   closing the tissue opening with the thermal device at the target site;
   after closing the tissue opening, applying or continuing to apply thermal therapy to the target site through the thermal device; and
   after closing the tissue opening, separating at least one of a fluid inlet conduit and a fluid outlet conduit from the thermal device by remote actuation
   wherein the thermal device comprises a malleable pad.

* * * * *